(12) United States Patent
Waisman et al.

(10) Patent No.: US 7,250,271 B2
(45) Date of Patent: Jul. 31, 2007

(54) ANTI-ANGIOGENESIS METHODS, COMPOSITIONS AND USES THEREFOR

(76) Inventors: David Waisman, 136 NW Silvergrove Manor, Calgary, Alberta (CA) T3B 5K6; Mijung Kwon, 10005-3131 Hospital Drive N.W., Calgary, Alberta (CA) T2N 2T8

(*) Notice: Subject to any disclaimer, the term of this patent is extended or adjusted under 35 U.S.C. 154(b) by 612 days.

(21) Appl. No.: 10/304,287

(22) Filed: Nov. 26, 2002

(65) Prior Publication Data

US 2003/0083234 A1     May 1, 2003

Related U.S. Application Data

(60) Provisional application No. 60/333,866, filed on Nov. 28, 2001.

(51) Int. Cl.
| | |
|---|---|
| C12P 21/06 | (2006.01) |
| C12N 9/50 | (2006.01) |
| C12N 15/00 | (2006.01) |
| C07K 1/00 | (2006.01) |
| C07H 21/04 | (2006.01) |

(52) U.S. Cl. ............... 435/69.1; 435/183; 435/219; 435/320.1; 530/350; 536/23.2

(58) Field of Classification Search ............... 435/69.1, 435/183, 219, 252.3, 320.1; 530/350; 536/23.2
See application file for complete search history.

(56) References Cited

U.S. PATENT DOCUMENTS 4,462,980 A    7/1984    Diedrichsen et al. ........ 424/1.1

FOREIGN PATENT DOCUMENTS

WO    WO 02/44328    6/2002

OTHER PUBLICATIONS

Soffa. Cancer Metastasis Rev. Jun. 2000; 19(1-2):97-107.*
Kassam et al. J Biol Chem. Feb. 20, 1998; 273(8):4790-4799.*
Kassam et al. Biochemistry. Dec. 1, 1998;37(48):16958-66.*
Kwon et al. J Biol Chem. Mar. 29, 2002;277(13):10903-10911.*
Kassam et al. J Biol Chem. Mar. 23, 2001; 276(12): 8924-8933.*
Gately et al. Proc. Natl. Acad. Sci. USA. Sep. 1997; 94: 10868-10872.*
Ballagamba et al., Tyrosine phosphorylation of annexin II tetramer is stimulated by membrane binding, *J. Biol. Chem.* 272: 3195-3199, Feb. 7, 1997.
Brooks et al., $Ca^{2+}$-dependent, phospholipids independent binding of annexin 2 to annexin 6, *Biochem. J.* manuscript No. BJ20020997, Jul. 25, 2002.
Cao et al., Kringle domains of human angiostatin, *J. Biol. Chem.* 271 29461-29467, Nov. 15, 1996.
Choi et al., Annexin II tetramer inhibits plasmin-dependent fibrinolysis, *Biochemistry* 31: 648-655, Jan. 13, 1998.

Choi et al., Regulation of plasmin-dependent fibrin clot lysis by annexin II heterotetramer, *J. Biol. Chem.* 276: 25212-25221, Jul. 6, 2001.
Falcone et al., Macrophage formation of angiostatin during inflammation, *J. Biol. Chem.* 273 31480-31485, Nov. 20, 1998.
Filipenko and Waisman, Characterization of the $Ca^{2+}$-binding sites of annexin II tetramer, *J. Biol. Chem.* 275: 38877-38884, Dec. 8, 2000.
Filipenko and Waisman, The C terminus of annexin II mediates binding to F-actin, *J. Biol. Chem.* 276: 5310-5315, Feb. 16, 2001.
Fitzpatrick et al., Regulation of plasmin activity by annexin II tetramer, *Biochemistry* 39: 1021-1028, Jan. 14, 2000.
Fitzpatrick et al., Fucidan-dependent conformational changes in annexin II tetramer, *Biochemistry* 39: 2140-2148, Feb. 10, 2000.
Fogg et al., The p11 subunit of annexin II heterotetramer is regulated by basic carboxypeptidase, *Biochemistry* 41: 4953-4961, Mar. 20, 2002.
Gately et al., The mechanism of cancer-mediated conversion of plasminogen to the angiogenesis inhibitor angiostatin, *PNAS* 94: 10868-10872, Sep. 1997.
Johnsson and Weber, Alkylation of cysteine 82 of p11 abolishes the complex formation with the tyrosine-protein kinase substrate p36, *J. Biol. Chem.* 265: 14464-14468, Aug. 25, 1990.
Kang et al., Characterization of human recombinant annexin II tetramer purified from bacteria: Role of N-terminal acetylation, *Biochemistry* 36: 2041-2050, Jan. 15, 1997.
Kassam et al., Characterization of the heparin binding properties of annexin II tetramer, *J. Biol. Chem.* 272: 15093-15100, Jun. 13, 1997.
Kassam et al., The role of annexin II tetramer in the activation of plasminogen, *J. Biol. Chem.* 273: 4790-4799, Feb. 20, 1998.
Kassam et al., The p11 subunit of the annexin II tetramer plays a key role in the stimulation of t-PA-dependent plasminogen activation, *Biochemistry* 37: 16958-16966, Nov. 5, 1998.
Kassam et al., Purification and characterization of $A_{61}$, *J. Biol. Chem.* 276: 8924-8933, Mar. 23, 2001.
Kwon et al., P22 is a novel plasminogen fragment with antiangiogenic activity, *Biochemistry* 40: 13246-13253, Oct. 13, 2001.
Kwon et al., Identification of annexin II heterotetramer as a plasmin reductase, *J. Biol. Chem.* 277: 10903-10911, Mar. 29, 2002.
Lay et al., Phosphoglycerate kinase acts in tumour angiogenesis as a disulphide reductase, *Nature* 408: 869-873, Dec. 14, 2000.
Stathakis et al., Generation of angiostatin by reduction and proteolysis of plasmin, *J. Biol. Chem.* 272: 20641-20645, Aug. 15, 1997.
Stathakis et al., Angiostatin formation involves disulfide bond reduction and proteolysis in kringle 5 of plasmin, *J. Biol. Chem.* 274: 8910-8916, Mar. 26, 1999.

(Continued)

*Primary Examiner*—Tekchand Saidha
*Assistant Examiner*—Christian L. Fronda

(57) ABSTRACT

This invention relates generally to methods of producing peptide-based anti-angiogenesis compounds using plasmin reductases, and specifically to methods of producing an $A_{61}$ anti-angiogenic plasmin fragment using an annexin II heterotetramer or subunit thereof. This invention also relates to anti-angiogenesis methods and compositions comprising a plasmin reductase or polynucleotides encoding subunits thereof. Compositions useful for the inhibition or promotion of angiogenesis are also disclosed.

6 Claims, 13 Drawing Sheets

OTHER PUBLICATIONS

Teratani et al., Induced transcriptional expression of calcium-binding protein S100A1 and S100A10 genes in human renal cell carcinoma, *Cancer Lett.* 175: 71-77, Jan. 2002.

Caplan et al, "Regulation of annexin A2 by reversible glutathionylation." J Biol Chem., 2004, vol. 279, No. 9, pp. 7740-7750.

Choi et al., "p11 regulates extracellular plasmin production and invasiveness of HT1080 fibrosarcoma cells." FASEB J., 2003, vol. 17, No. 2, pp. 235-246.

Filipenko et al., "Annexin A2 is a novel RNA-binding protein." J Biol Chem., 2004, vol. 279, No. 10, pp. 8723-8731

Fitzpatrick et al., "Regulation of plasmin activity by annexin II tetramer." Biochemistry, 2000, vol. 39, No. 5, pp. 1021-1028.

Heidtmann et al., "Generation of angiostatin-like fragments from plasminogen by prostate-specific antigen." Br J Cancer, 1999, vol. 81, No. 8, pp. 1269-1273.

MacDonald et al., "The tumor-suppressing activity of angiostatin protein resides within kringles 1 to 3." Biochem Biophys Res Commun., 1999, vol. 264, No. 2, pp. 469-477.

MacLeod et al., "Phospholipid-associated annexin A2-S100A10 heterotetramer and its subunits: characterization of the interaction with tissue plasminogen activator, plasminogen, and plasmin." J Biol Chem., 2003, vol. 278, No. 28, pp. 25577-25584.

Menhart et al., "Construction, expression, and purification of recombinant kringle 1 of human plasminogen and analysis of its interaction with omega-amino acids." Biochemistry, 1991, vol. 30, No. 7, pp. 1948-1957.

Yao et al., "Dexamethasone alters arachidonate release from human epithelial cells by induction of p11 protein synthesis and inhibition of phospholipase A2 activity." J Biol Chem., 1999, vol. 274, No. 24, pp. 17202-17208.

Zhang et al., "RNA interference-mediated silencing of the S100A10 gene attenuates plasmin generation and invasiveness of Colo 222 colorectal cancer cells." J Biol Chem., 2004, vol. 279, No. 3, pp. 2053-2062.

* cited by examiner

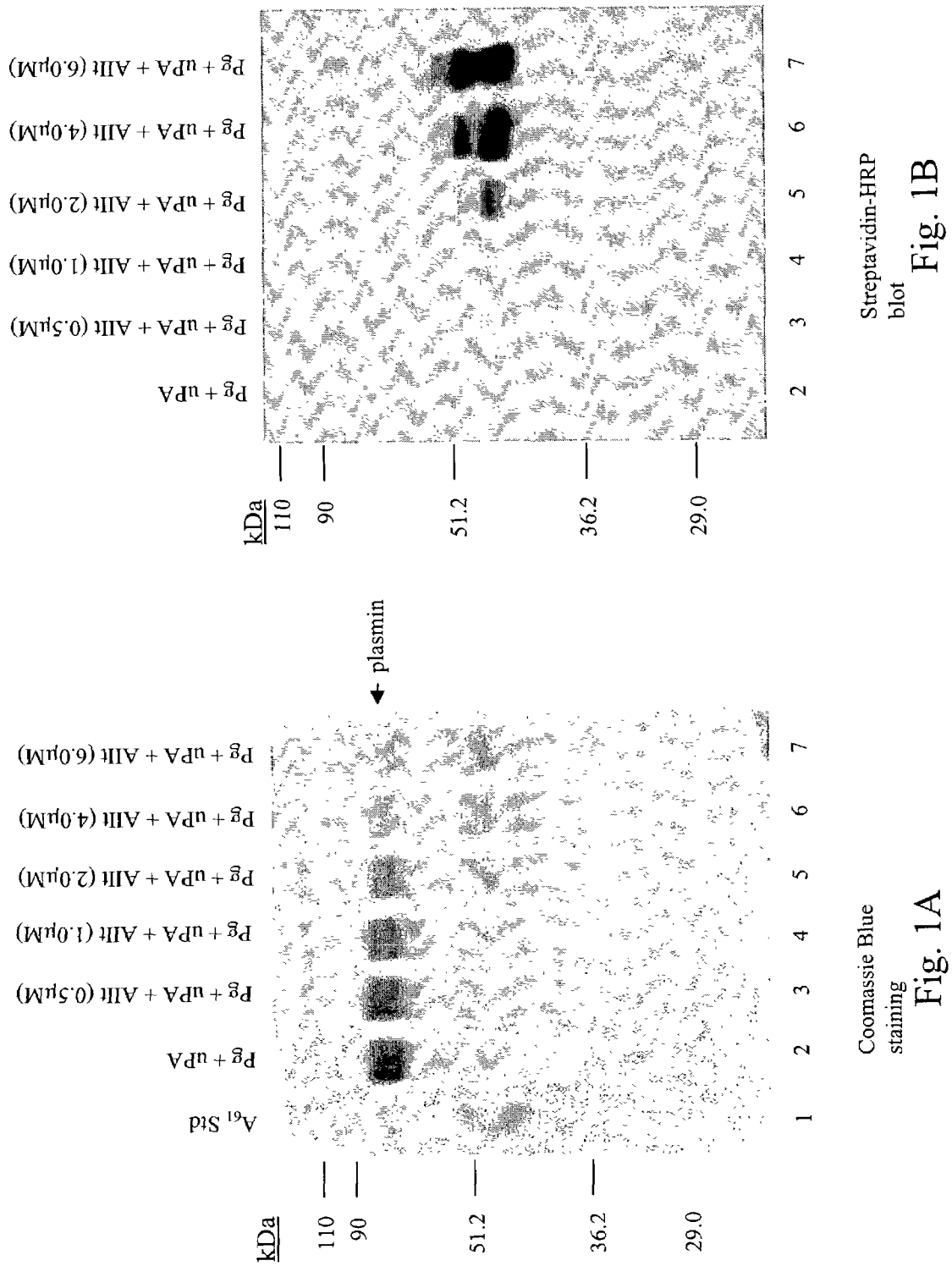

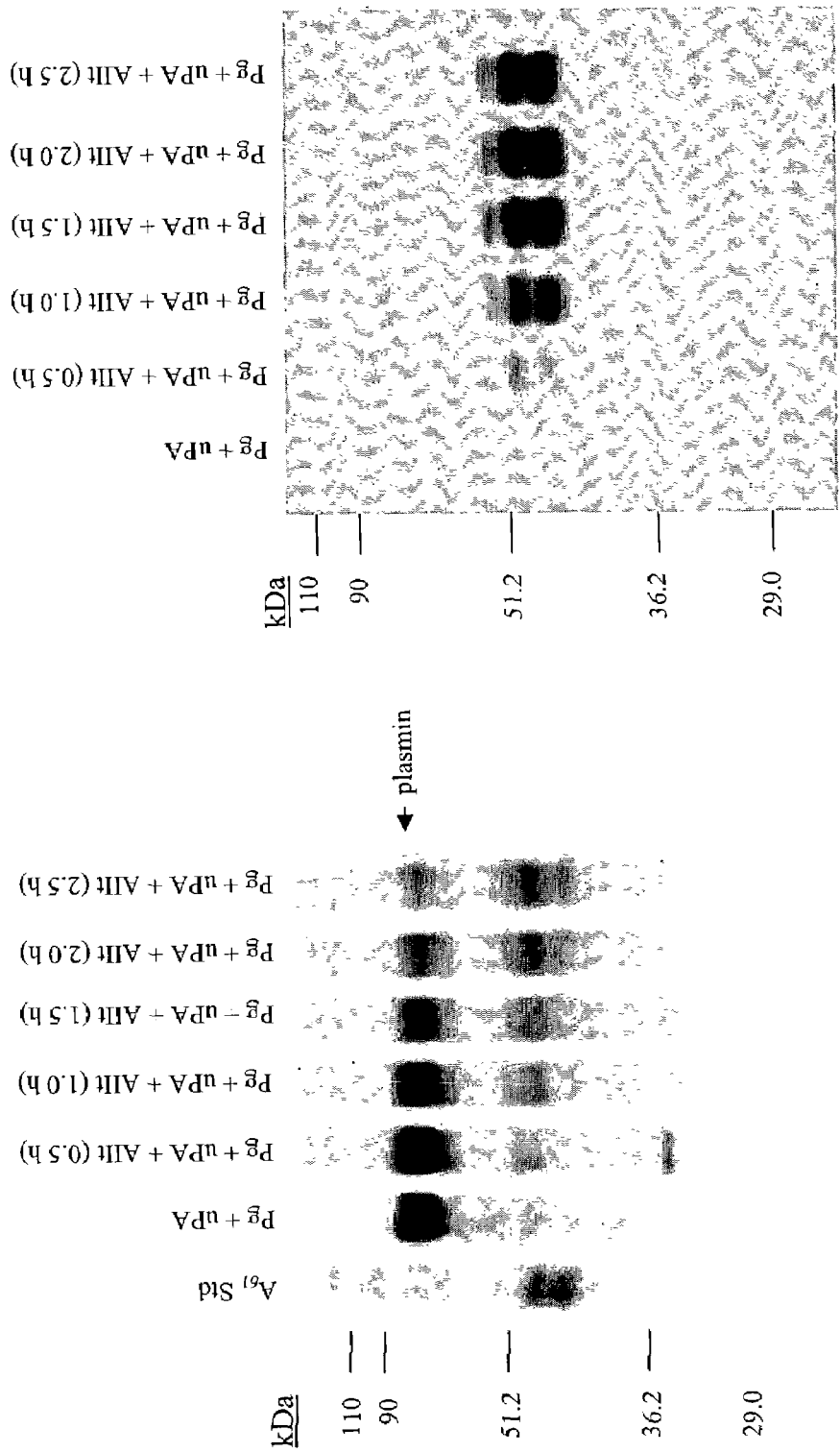

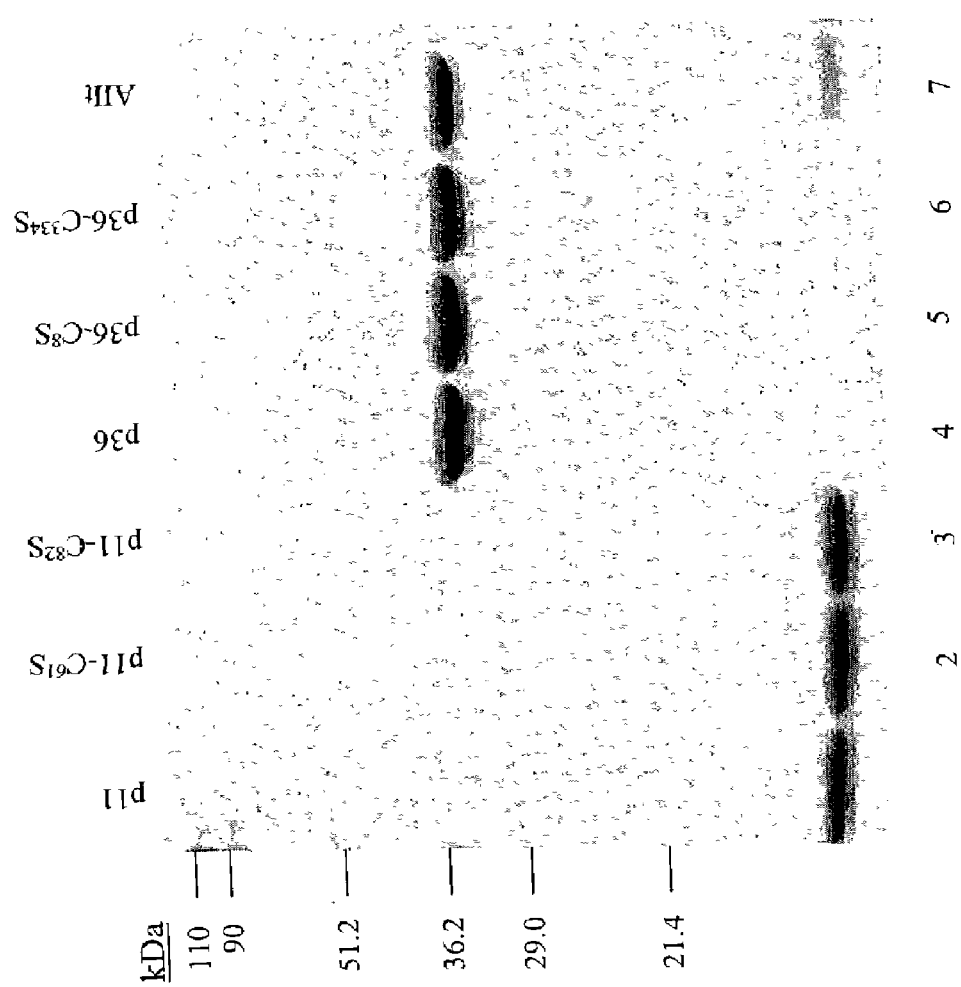

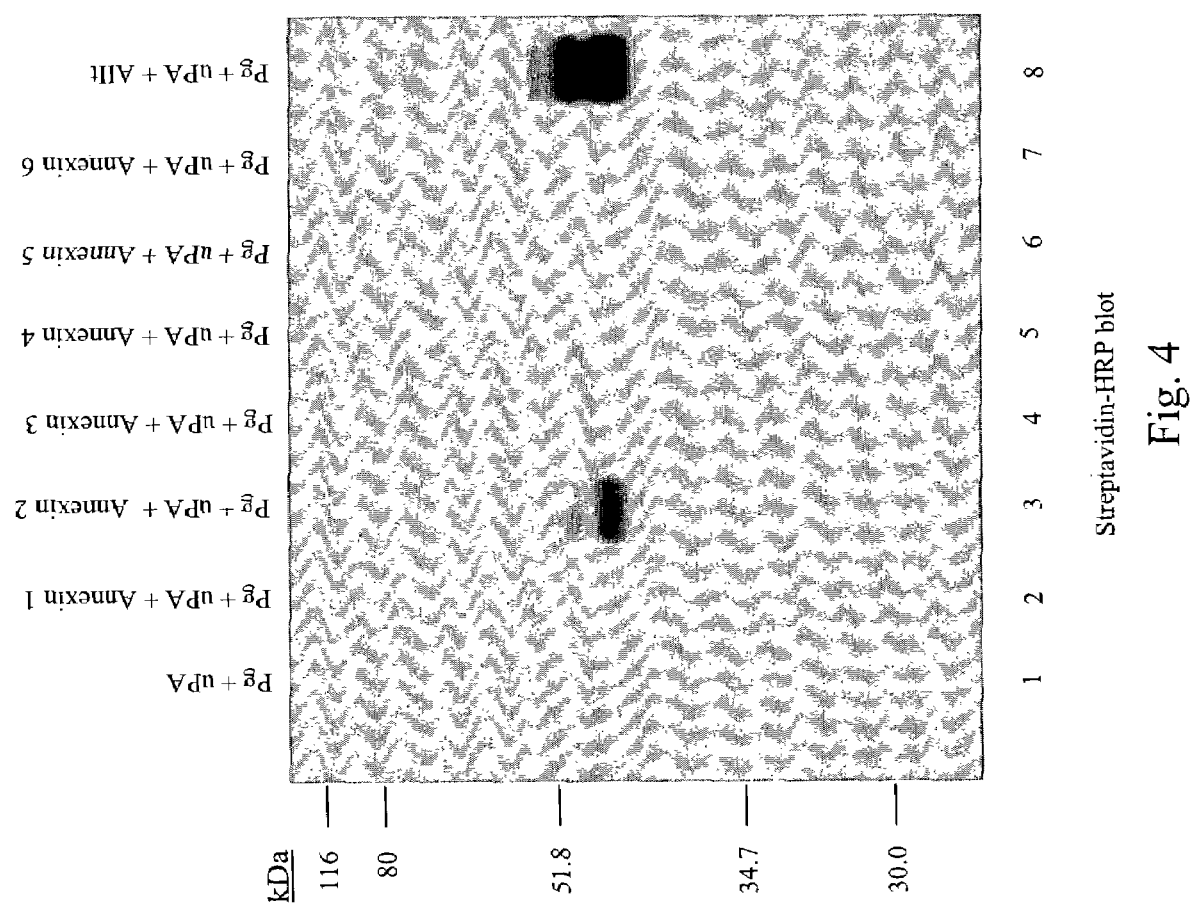

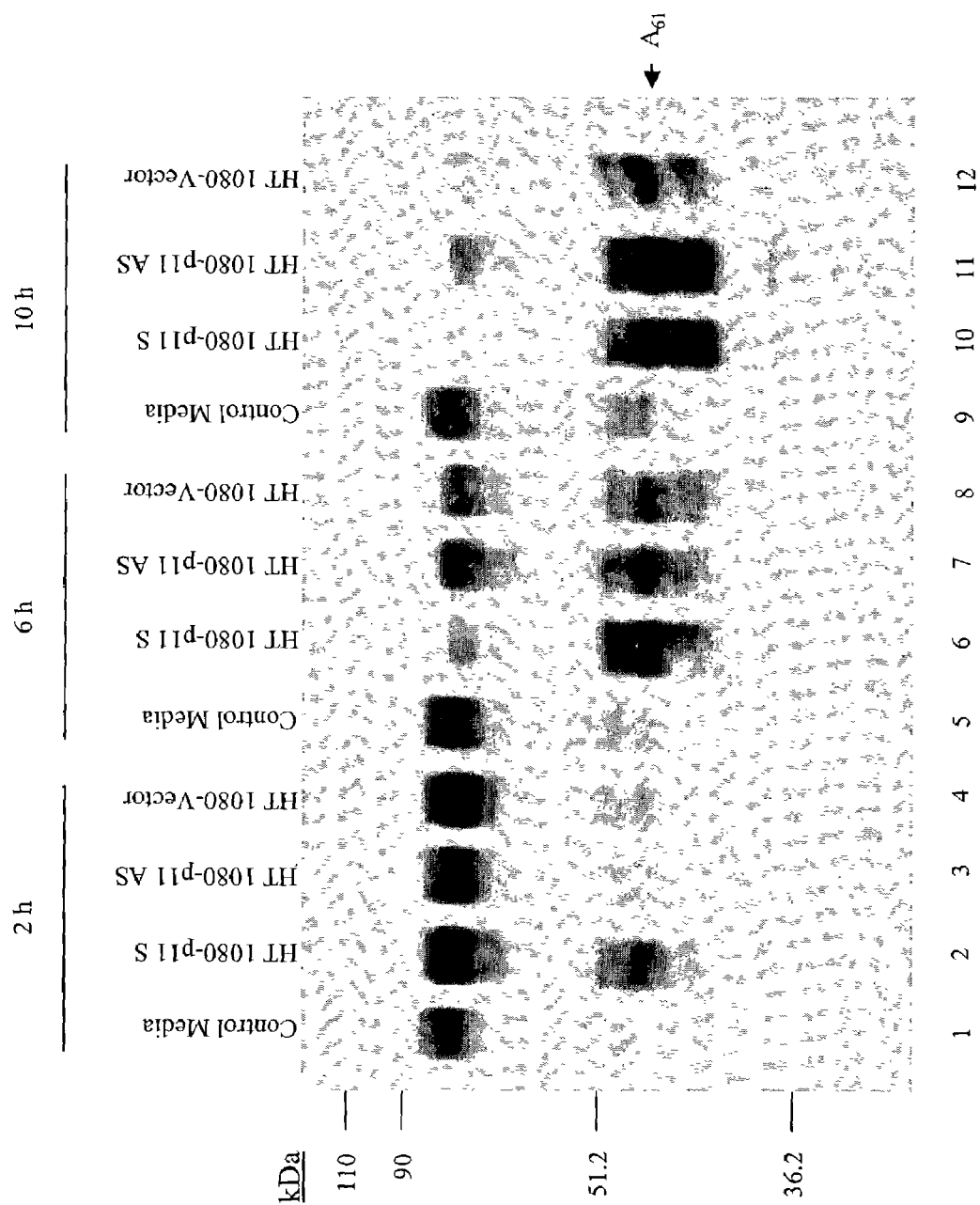

ANTI-ANGIOGENESIS METHODS, COMPOSITIONS AND USES THEREFOR

PARENT CASE TEXT

This application claims benefit of priority to U.S. Provisional Patent Application No. 60/333,866, filed Nov. 28, 2001.

GOVERNMENT SUPPORT

This work was supported in part by a grant from the National Institutes of Health (CA78639). The United States Government has certain rights in this invention.

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f). The sequence listing contains sequences, which serve to illustrate the art-recognized plasmin/plasminogen amino acid number system, and which are not meant to limit the scope of the invention to those particular sequences. Other plasmin/plasminogen sequences, as well as p36 and p11 sequences are known in the art and can be readily obtained by one skilled in the art.

BACKGROUND OF THE INVENTION

1. Field of the Invention

This invention relates to methods of producing peptide-based anti-angiogenesis compounds using plasmin reductases, and specifically to methods of producing an $A_{61}$ anti-angiogenic plasmin fragment using an annexin II heterotetramer. This invention also relates to compositions and methods useful for modulating angiogenesis.

2. Description of the Related Art

The following references listed below as part of this paragraph are cited throughout this disclosure using the associated numerical identifiers. Applicant makes no statement, inferred or direct, regarding the status of these references as prior art. These references are incorporated herein by reference:

1. O'Reilly, M. S., Holmgren, L., Shing, Y., Chen, C., Rosenthal, R. A., Cao, Y., Moses, M., Lane, W. S., Sage, E. H., and Folkman, J. (1994) *Cold Spring Harb. Symp. Quant. Biol.* 59, 471-482
2. Dong, Z., Kumar, R., Yang, X., and Fidler, I. J. (1997) *Cell* 88, 801-810
3. Falcone, D. J., Khan, K. F., Layne, T., and Fernandes, L. (1998) *J. Biol. Chem.* 273, 31480-31485
4. Gately, S., Twardowski, P., Stack, M. S., Patrick, M., Boggio, L., Cundiff, D. L., Schnaper, H. W., Madison, L., Volpert, O., Bouck, N., Enghild, J., Kwaan, H. C., and Soff, G. A. (1996) *Cancer Res.* 56, 4887-4890
5. Gately, S., Twardowski, P., Stack, M. S., Cundiff, D. L., Grella, D., Castellino, F. J., Enghild, J., Kwaan, H. C., Lee, F., Kramer, R. A., Volpert, O., Bouck, N., and Soff, G. A. (1997) *Proc. Natl. Acad. Sci. U.S.A.* 94, 10868-10872
6. Stathakis, P., Lay, A. J., Fitzgerald, M., Schlieker, C., Matthias, L. J., and Hogg, P. J. (1999) *J. Biol. Chem.* 274, 8910-8916
7. Patterson, B. C. and Sang, Q. A. (1997) *J. Biol. Chem.* 272, 28823-28825
8. Cornelius, L. A., Nehring, L. C., Harding, E., Bolanowski, M., Welgus, H. G., Kobayashi, D. K., Pierce, R. A., and Shapiro, S. D. (1998) *J. Immunol.* 161, 6845-6852
9. Lijnen, H. R., Ugwu, F., Bini, A., and Collen, D. (1998) *Biochemistry* 37, 4699-4702
10. Morikawa, W., Yamamoto, K., Ishikawa, S., Takemoto, S., Ono, M., Fukushi, J., Naito, S., Nozaki, C., Iwanaga, S., and Kuwano, M. (2000) *J. Biol. Chem.*
11. Heidtmann, H. H., Nettelbeck, D. M., Mingels, A., Jager, R., Welker, H. G., and Kontennann, R. E. (1999) *Br. J. Cancer* 81, 1269-1273
12. O'Reilly, M. S., Wiederschain, D., Stetler-Stevenson, W. G., Folkman, J., and Moses, M. A. (1999) *J. Biol. Chem.* 274, 29568-29571
13. Wu, H. L., Shi, G. Y., Wohl, R. C., and Bender, M. L. (1987) *Proc. Natl. Acad. Sci. U.S.A.* 84, 8793-8795
14. Kassam, G., Kwon, M., Yoon, C. -S., Graham, K. S., Young, M. K., Gluck, S., and Waisman, D. M. (2001) *J. Biol. Chem.* 276, 8924-8933
15. Stathakis, P., Fitzgerald, M., Matthias, L. J., Chesterman, C. N., and Hogg, P. J. (1997) *J. Biol. Chem.* 272, 20641-20645
16. Lay, A. J., Jiang, X. M., Kisker, O., Flynn, E., Underwood, A., Condron, R., and Hogg, P. J. (2000) *Nature* 408, 869-873
17. Kassam, G., Choi, K. S., Ghuman, J., Kang, H. M., Fitzpatrick, S. L., Zackson, T., Zackson, S., Toba, M., Shinomiya, A., and Waisman, D. M. (1998) *J. Biol. Chem.* 273, 4790-
18. Kassam, G., Le, B. H., Choi, K. S., Kang, H. M., Fitzpatrick, S. L., Louie, P., and Waisman, D. M. (1998) *Biochemistry* 37, 16958-16966
19. Fitzpatrick, S. L., Kassam, G., Choi, K. S., Kang, H. -M., Fogg. D. K., and Waisman, D. M. (2000) *Biochemistry* 39, 1021-1028
20. Kang, H. M., Choi, K. S., Kassam, G., Fitzpatrick, S. L., Kwon, M., and Waisman, D. M. (1999) *Trends. Cardiovasc. Med.* 9, 92-102
21. Khanna, N. C., Heiwig, E. D., Ikebuchi, N. W., Fitzpatrick, S., Bajwa, R., and Waisman, D. M. (1990) *Biochemistry* 29, 4852-4862
22. Filipenko, N. R. and Waisman, D. M. (2001) *J. Biol. Chem.* 276, 5310-5315
23. Ayala-Sanmartin, J., Vincent, M., Sopkova, J., and Gallay, J. (2000) *Biochemistry* 39, 15179-15189
24. Ghahary, A., Tredget, E. E., Chang, L. J., Scott, P. G., and Shen, Q. (1998) *J Invest Dermatol.* 110, 800-805
25. Johnsson, N. and Weber, K. (1990) *J. Biol. Chem.* 265, 14464-14468
26. Mai, J., Waisman, D. M., and Sloane, B. F. (2000) *Biochim. Biophys. Acta* 1477, 215-230
27. Rubartelli, A., Bajetto, A., Allavena, G., Wolhman, E., and Sitia, R. (1992) *J. Biol. Chem.* 267, 24161-24164
28. Terada, K., Manchikalapudi, P., Noiva, R., Jauregui, H. O., Stockert, R. J., and Schilsky, M. L. (1995) *J. Biol. Chem.* 270, 20410-20416
29. Soderberg, A., Sahaf, B., and Rosen, A. (2000) *Cancer Res.* 60, 2281-2289
30. Heuck, A. P. and Wolosiuk, R. A. (1997) *J. Biochem. Biophys. Methods* 34, 213-225
31. Heuck, A. P. and Wolosiuk, R. A. (1997) *Anal. Biochem.* 248, 94-101
32. Lahav, J., Gofer-Dadosh, N., Luboshitz, J., Hess, O., and Shaklai, M. (2000) *FEBS Lett.* 475, 89-92

33. Langenbach, K. J. and Sottile, J. (1999) *J. Biol. Chem.* 274, 7032-7038
34. Essex, D. W. and Li, M. (1999) *Br. J. Haematol.* 104, 448-454
35. Mayadas, T. N. and Wagner, D. D. (1992) *Proc. Natl. Acad. Sci. U.S.A* 89, 3531-3535
36. O'Neill, S., Robinson, A., Deering, A., Ryan, M., Fitzgerald, D. J., and Moran, N. (2000) *J. Biol. Chem.* 275, 36984-36990

Annexin II heterotetramer ("AIIt") is a $Ca^{2+}$-binding protein complex that binds tPA, plasminogen and plasmin and stimulates both the formation and autoproteolysis of plasmin at the cell surface (17-19) (reviewed in (20)). The protein consists of two copies of an annexin II 36 kDa subunit (p36) called annexin II and two copies of an 11 kDa subunit (p11) called S100A10. It is known in the art that the carboxyl-terminal lysines of the p11 subunit plays a key role in plasminogen binding and activation (18).

Angiostatin was originally identified in the urine of mice bearing Lewis lung carcinoma (LLC) as a 38 kDa proteolytically-derived fragment of plasminogen which encompassed the first four kringle domains of plasminogen ($Lys^{78}$-$Ala^{440}$ according to SEQ ID NO:1). Angiostatin was shown to be a potent antiangiogenic protein that inhibited the growth of human and murine carcinomas and also induced dormancy in their metastases. Angiostatin was also characterized as a specific antiangiogenic protein that blocked microvascular endothelial cell proliferation but not the proliferation of nonendothelial cells (1).

Angiostatin is a member of a family of antangiogenic plasminogen fragments ("AAPFs"). Physiologically relevant AAPFs include a 38 kDa AAPF isolated from the conditioned media of tumor-infiltrating mnacrophages (2), a 43 kDa and 38 kDa AAPF identified in the conditioned media of Chinese hamster ovary and HT1080 fibrosarcoma cells and a 48 kDa AAPF present in macrophage conditioned media (3). Other AAPFs include a 43 kDa and a 38 kDa AAPF isolated from the conditioned media of human prostrate carcinoma PC-3 cells (4; 5) and AAPFs of 66, 60 and 57 kDa detected in the conditioned media of HT1080 and Chinese hamster ovary cells (6). Since the carboxyl-terminus of most of these AAPFs was not determined, the exact primary sequence of most of the AAPFs is unknown.

Two distinct pathways have been identified for the formation of AAPFs. First, certain proteinases can directly cleave plasminogen into AAPFs. These proteinases include metalloelastase, gelatinase B (MMP-9), stromelysin-1 (MMP-3), matrilysin (MMP-7), cathepsin D and prostate-specific antigen (7-11). The source of these proteinases may be tumor-infiltrating macrophages (2) or the cancer cells themselves. For example, the conversion of plasminogen to angiostatin by macrophages is dependent on the release of metalloelastase from these cells. In comparison, Lewis lung carcinoma cells release MMP-2 which also cleaves plasminogen to angiostatin (12). Second, AAPFs are also generated by a three step mechanism which involves the conversion of plasminogen to plasmin by urokinase-type plasminogen activator ("uPA"), the autoproteolytic cleavage of plasmin and the release of the resultant plasmin fragment by cleavage of disulfide bonds. The cleavage of the plasmin disulfide bonds can be accomplished by free sulthydryl group donors (FSD) such as glutathione or by hydroxyl ions at alkaline pH (4; 5; 13; 14). Alternatively, the plasmin disulfide bonds can be cleaved enzymatically by a plasmin reductase such as phosphoglycerate kinase (15; 16).

In co-pending patent application PCT/US01/44515 (published as WO0244328 A and reference 14), which is incorporated herein by reference, it was shown that the primary AAPF present in mouse and human blood has a molecular weight of 61 kDa. This AAPF, called $A_{61}$, was produced in a cell-free system consisting of uPA and plasminogen. A, was shown to be a novel four-kringle containing plasminogen fragment consisting of the amino acid sequence, $Lys^{78}$ - $Lys^{468}$ (SEQ ID NO:1) (14). The release of $A_{61}$ from plasmin required cleavage of the $Lys^{468}$-$Gly^{469}$ (SEQ ID NO:1) bond by plasmin autoproteolysis and also cleavage of the $Cys^{462}$ - $Cys^{541}$ (SEQ ID NO:1) disulfide. Since $A_{61}$ was generated in a cell-free system from plasmin at alkaline pH in the absence of sulfhydryl donors, it was concluded that cleavage of the $Cys^{462}$-$Cys^{541}$ disulfide was catalyzed by hydroxyl ions in vitro. In contrast, at physiological pH, it was observed that the conversion of plasminogen to Al was very slow. These results contrasted with the observation that at physiological pH, HT1080 fibrosarcoma and bovine capillary endothelial (BCE) cells stimulated the rapid formation of $A_{61}$. Heretofore, the mechanism by which these cells stimulated plasmin reduction and the release of $A_{61}$ from plasmin was unclear.

SUMMARY OF THE INVENTION

According to the present invention, it was discovered that an annexin II heterotetramer or its subunits stimulates the conversion of plasminogen to $A_{61}$ in vitro. It was also discovered that an annexin II heterotetramer or its subunits (p36, p11) possesses an intrinsic plasmin reductase activity, and that the cysteinyl residues of both subunits of the annexin II heterotetramer (i.e., p36 and p11) participate in the reduction of plasmin. Preferred Annexins include annexin II (p36) and AIIt. The invention is also drawn to inhibitors of AIIt activity, which diminish $A_{61}$ production by cells. Preferred inhibitors of AIIt activity include antisense nucleotides, which down-regulate expression of AIIt on the surface of cells.

The present invention is drawn to a method of producing an anti-angiogenesis plasmin fragment comprising contacting a plasminogen polypeptide with a plasminogen activator and a plasmin reductase, wherein a reduced plasmin protein is produced. The anti-angiogenesis plasmin fragment, which has anti-angiogenesis activity, is released from the reduced plasmin protein. Preferably but not exclusively, the plasminogen activator is a urokinase-type plasminogen activator, a plasmin reductase is an annexin II heterotetramer, annexin II p36 subunit, or p11 and the anti-angiogenesis plasmin fragment is an $A_{61}$ corresponding to SEQ ID NO:7 or SEQ ID NO:8.

In another embodiment, the present invention is drawn to a method of producing an anti-angiogenesis plasmin fragment comprising contacting a plasmin protein with a plasmin reductase, wherein the anti-angiogenesis plasmin fragment, which has anti-angiogenesis activity, is released from a reduced plasmin protein. Preferably but not exclusively, the plasmin reductase is an annexin II heterotetramer, annexin II p36 subunit, or p11, and the anti-angiogenesis plasmin fragment is an $A_{61}$ corresponding to SEQ ID NO:7 or SEQ ID NO:8.

In another embodiment, the present invention is drawn to a method of inhibiting the formation of an $A_{61}$ anti-angiogenesis fragment comprising contacting a cell with a polynucleotide, wherein (a) the polynucleotide encodes a p11 antisense polynucleotide, which enters the cell inhibits the expression of p11 on the surface of the cell, and (b) expression of p11 is requited for efficient production of the $A_{61}$ anti-angiogenesis fragment.

In another embodiment, he present invention is drawn to a method of increasing the formation of an $A_{61}$ anti-angiogenesis fragment comprising contacting a cell with a polynucleotide, wherein (a) the polynucleotide encodes a p11 sense polynucleotide, which enters the cell increases the expression of p11 subunits on the surface of the cell, and (b) expression of p11 is required for efficient production of the $A_{61}$ anti-angiogenesis fragment.

BRIEF DESCRIPTION OF THE DRAWINGS

FIG. 1 illustrates the stimulation of conversion of plasminogen to $A_{61}$ by AIIt. (A,B) AIIt dose-dependent generation of $A_{61}$. [Glu]-plasrrinogen (4 μM) was incubated with u-PA (0.075 μM) and various concentrations of AIIt, then subjected to non-reduced SDS-PAGE followed by Coomassie blue staining (A). Portions of the reaction mixtures were incubated with MPB (100 μM), reduced glutathione (200 μM), iodoacetamide (400 μM), L-lysine-Sepharose, and then subjected to non-reduced SDS-PAGE followed by Western blot with streptavidin-HRP (B). (C,D) Time-course generation of $A_{61}$. [Glu]-plasminogen (4 μM) was incubated with uPA (0.075 μM) and AIIt (4 μM) for various times at 37°. The results are shown as Coomassie blue staining (C) and Western blot with streptavidin-HRP (D).

FIG. 4 illustrates the specificity of the plasmin reductase activity of AIIt. [Glu]-plasminogen (4 μM) was incubated with uPA (0.075 μM) and the indicated annexin proteins (4 μM). The result shown is a Western blot with streptavidin-HRP.

DETAILED DESCRIPTION OF THE INVENTION

The inventors have discovered that an annexin II heterotetramer or its subunits (p36, p11), contains an intrinsic plasmin reductase activity and is useful in the generation of the antiangiogenic plasminogen fragment, $A_{61}$, which is a four-kringle containing plasminogen fragment comprising the amino acid sequence $Lys^{78}$-$Lys^{468}$, wherein the numbering of $Lys^{78}$-$Lys^{468}$ is based upon the numbering of SEQ ID NO:1. It is also disclosed that cells transduced with a vector encoding a p11 antisense RNA ("antisense p11") show reduced extracellular AIIt and $A_{61}$ production, demonstrating the utility of AIIt as an antiangiogenic agent and in the formation of other antiangiogenic agents.

Figure 8:
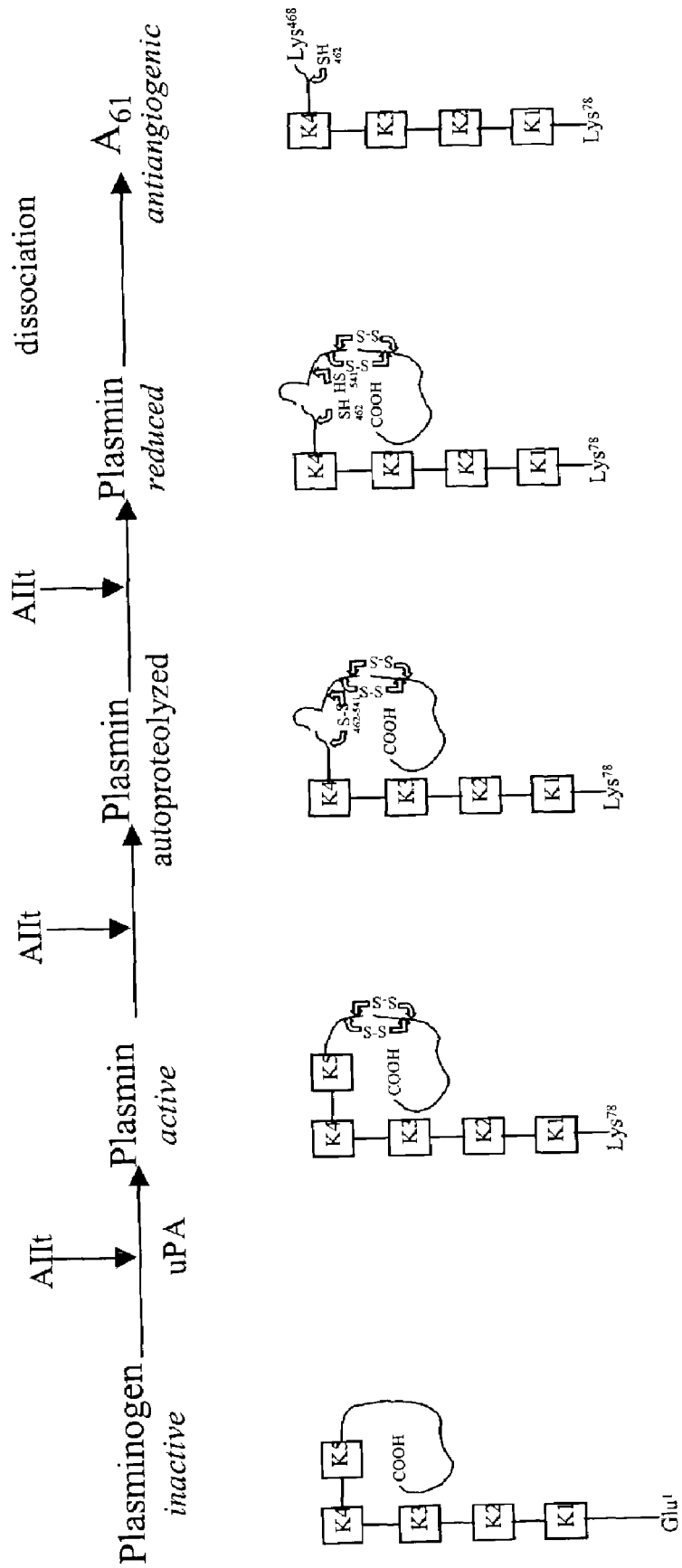
FIG. 8 diagrammatically illustrates the mechanism of $A_{61}$ formation. K represents the kringle domain of plasminogen. S—S indicates the disulfide bond and SH represents the free thiol generated. Plasmin catalyzes the cleavage of the $Lys^{77}$-$Lys^{78}$ and Lys469-$Gly^{469}$ bonds of plasmninogen.

While not intending to be bound by theory, the inventors postulate that plasminogen is converted to $A_{61}$ in a three-step process FIG. 8). First, u-PA cleaves the Arg561-$Val^{562}$ of plasminogen (SEQ ID NO:1) resulting in the formation of plasmin. Second, plasmin autoproteolysis results in the cleavage of the $Lys^{77}$-$Lys^{78}$ and $Lys^{468}$-$Gly^{469}$ bond. A minor cleavage site at $Arg^{471}$-$Gly^{472}$ has also been shown to be present (minor $A_{61}$ fragment depicted in SEQ ID NO:8). However, the presence of a $Cys^{462}$-$Cys^{541}$ disulfide prevents release of $A_{61}$ ($Lys^{78}$-$Lys^{468}$). Third, AIIt catalyzes the reduction of the $Cys^{462}$-$Cys^{54}$1 disulfide which allows the release of $A_{61}$ (SEQ ID NO:7, major form) from the rest of the molecule. Since AIIt does not reduce catalytically inactive plasmin, one skilled in the art may conclude that plasmin autoproteolysis must occur before plasmin reduction, suggesting that autoproteolyzed plasmin is the substrate for AIIt's plasmin reductase activity.

It is herein disclosed that plasmin autoproteolysis precedes plasmin reduction and that plasmin reduction is accelerated by AIIt. The AIIt present at the surface of certain cells participates in the conversion of plasminogen to $A_{61}$ and loss of extracellular AIIt results in the inhibition of cell-generated $A_{61}$. AIIt likely functions as a catalyst, since large amounts of plasminogen are converted to $A_{61}$ by AIIt expressing cells. This suggests that in order for AIIt to continually reduce plasmin it must proceed through cycles of oxidation by plasmin and reduction by unknown reducing equivalents. The mechanism by which oxidized extracellular AIIt is reduced is unknown at this time.

It is further disclosed that both the p36 and p11 subunits of AIIt possess plasmin reductase activity. In the case of the p36 subunit the $Cys^{334}$ residue (the cysteine at position number 334 according to SEQ ID NO:2) is essential for plasmin reductase activity. In the case of the p11 subunit both $Cys^{61}$ and $Cys^{82}$ (according to SEQ ID NO:3) are capable of participating in plasmin reduction. Although speculative, the simplest explanation for these observations is that plasmin and autoproteolyzed plasmin can bind to AIIt but the unique conformational change induced by the binding of autoproteolyzed plasmin to AIIt may result in an increased accessibility of cysteinyl residues of AIIt, which participate in reduction of autoproteolyzed plasmin. Since, according to the examples presented below, $Cys^{334}$ of p36 was not labeled with the thiol specific reagent MPB, $Cys^{334}$ of p36 is likely shielded from the solvent. Furthermore, a p36 mutant, which comprises a Cys to Ser substitution at position 334, is inactive in terms of plasmin reductase activity. It is therefore reasonable for one skilled in the art to suspect that $Cys^{334}$ may be shielded and only accessible for reduction of plasmin upon binding of autoproteolyzed plasmin to AIIt.

Protein disulfide reductases typically contain the Cys-X-X-Cys motif in their active sites. Members of this family of proteins include thioredoxin, protein disulfide isomerase, fibronectin, von Willebrand factor and platelet integrin $\alpha_{IIb}\beta_3$ (28;29;32-36). Typically these proteins share the general property of catalyzing the reduction of insulin disulfides. In contrast, AIIt does not contain the Cys-X-X-Cys motif and does not catalyze the reduction of insulin disulfides. This suggests that the intrinsic plasmin reductase activity of AIIt is due to a novel mechanism of disulfide reduction.

The phrase "anti-angiogenesis plasmin fragment" ("AAPF"), as used herein, means a polypeptide fragment of plasminogen or plasmin, which inhibits the recruitment or growth of blood vessels, or the recruitment or growth of endothelial cells, wherein the plasminogen or plasmin may be from any species of metazoan. For example, AAPFs include, p22 and $A_{61}$ (WO0244328 A and reference 14), a 38 kDa AAPF isolated from the conditioned media of tumor-infiltrating macrophages (2), a 43 kDa and 38 kDa AAPF identified in the conditioned media of Chinese hamster ovary and HT1080 fibrosarcoma cells, a 48 kDa AAPF present in macrophage conditioned media (3), a 43 kDa and a 38 kDa AAPF isolated from the conditioned media of human prostrate carcinoma PC-3 cells (4;5) and AAPFs of 66, 60 and 57 kDa detected in the conditioned media of HT1080 and Chinese hamster ovary cells (6). Preferred AAPFs include $A_{61}$.

The term "plasmin protein" means any plasmin protein, which includes active plasmin polypeptide, proteolyzed plasmin, and reduced plasmin, from any species. A preferred plasmin protein has an N-terminal lysine, which corresponds to $Lys^{78}$ of plasminogen.

The phrase "plasminogen activator" means an enzyme that catalyzes the proteolysis of a plasminogen polypeptide to produce an active plasmin protein. Preferred plasminogen activators include urokinase-type plasminogen activators (uPA), streptokinase and tissue-type plasminogen activators (tPA).

The phrase "plasmin reductase" means an agent, preferably a protein, which is capable of catalyzing the reduction of disulfide bridges of a plasminogen polypeptide or plasmin protein. Preferred plasmin reductases include annexin II heterotetramer (used interchangeably with "annexin II tetramer" or "AIIt"), annexin II p36 subunit ("p36"), S100A10 subunit ("p11"), thioredoxin and protein disulfide isomerase.

The phrase "anti-angiogenesis activity" means (a) the ability of a substance to inhibit endothelial cell proliferation or migration, (b) kill proliferating endothelial cells, or (c) the ability of a substance to inhibit the formation of new blood vessels in a tissue. Preferred substances are peptides such as $A_{61}$. Preferred $A_{61}$ polypeptides have a sequence as set forth in SEQ ID NO:7 or SEQ ID NO:8. The term "angiogenesis" means the formation of new blood vessels in a tissue, the stimulation of endothelial cells to proliferate, or the promotion of survival of proliferating endothelial cells.

The phrase "p11 antisense polynucleotide" means a single stranded RNA molecule, which is complementary to a p11 RNA that can be translated to produce a p11 polypeptide, or a fragment thereof. Functionally, a p11 antisense polynucleotide is capable of decreasing the expression of p11 protein in a cell. A preferred p11 antisense polynucleotide may be a DNA or RNA as set forth in SEQ ID NO:5. The inventors also envision that a siRNA (small interfering RNA) comprising a p11 sequence, which in preliminary experiments suggests that it is effective in decreasing the expression of p11 in a cell, may be useful in stimulating angiogenesis in a tissue, such as in myopathological heart tissue.

The phrase "p11 sense polynucleotide" means a single stranded RNA molecule, which is can be translated to produce a p11 polypeptide, or a fragment thereof. Functionally, a p11 antisense polynucleotide is capable of increasing the expression of p11 protein in a cell. A preferred p11 sense polynucleotide may be a DNA or RNA as set forth in SEQ ID NO:6. The terms "p11", "p11 polypeptide", "p11 protein", "p11 subunit", "annexin II p11", "annexin II p11 subunit", "S100A10", and "S100A10 subunit" are equivalent and are used interchangeably throughout the instant specification and claims.

The term "vector" refers to a polynucleotide that enables the expression of a constituent polynucleotide in a cell, wherein expression means the transcription of DNA into a RNA. Preferred vectors include retroviral vectors, such as pLin.

EXAMPLE 1

Stimulation of $A_{61}$ Production $A_{61}$ is an internal fragment of plasminogen that encompasses the sequence $Lys^{78}$-$Lys^{468}$ (SEQ ID NO: 1). The release of $A_{61}$ from plasmin is facilitated by the reduction of the $Cys^{462}$-$Cys^{541}$ disulfide bond of plasmin. Therefore, the release of A1 generates a free sulfhydryl residue at $Cys^{462}$. Since plasminogen and plasmin contain only disulfides, $A_{61}$ can be discriminated from these proteins on the basis of its reactivity with free sulfhydryl-reactive reagents such as 3-(N-raleidylpropionyl)biocytin (MPB). The reaction of free-sulfhydryl-containing proteins with MPB results in the biotinylation of the protein which allows easy detection with streptavadin-HRP.

As shown in FIG. 1A (lane 2), the incubation of uPA with plasminogen resulted in the generation of plasmin. As expected, the plasmin generated by this reaction did not contain a free cysteinyl residue and therefore did not react with MPB (FIG. 1B, lane 2). However, the addition of AIIt to the u-PA-plasminogen reaction resulted in the appearance of A6, (which displays a single major band and two minor bands of about $M_r$ 50 K on non-reduced SDS-PAGE) and disappearance of plasmin (FIG. 1A). Furthermore, the $A_{61}$ generated in these reactions reacted with MPB, confirming the presence of a free sulfhydryl in $A_{61}$ (FIG. 1B).

AIIt stimulated the dose- and time-dependent conversion of plasminogen to $A_{61}$ (FIGS. 1A-D). The maximal conversion of plasminogen to $A_{61}$ occurred at approximately equimolar concentrations of AIIt and plasminogen (FIGS. 1A,B). At equimolar concentrations the half-maximal conversion of plasminogen to $A_{61}$ occurred between 30-60 min (FIGS. 1C,D). Since AIIt stimulated the generation of $A_{61}$ in the absence of sulfhydryl donors, the data reasonably suggest that AIIt promoted the cleavage of a plasmin disulfide, presumably the $Cys^{462}$-$Cys^{541}$ disulfide, resulting in the release of $A_{61}$ from plasmin and the generation of a free cysteine ($Cys^{462}$) in $A_{61}$.

Figure 2A:
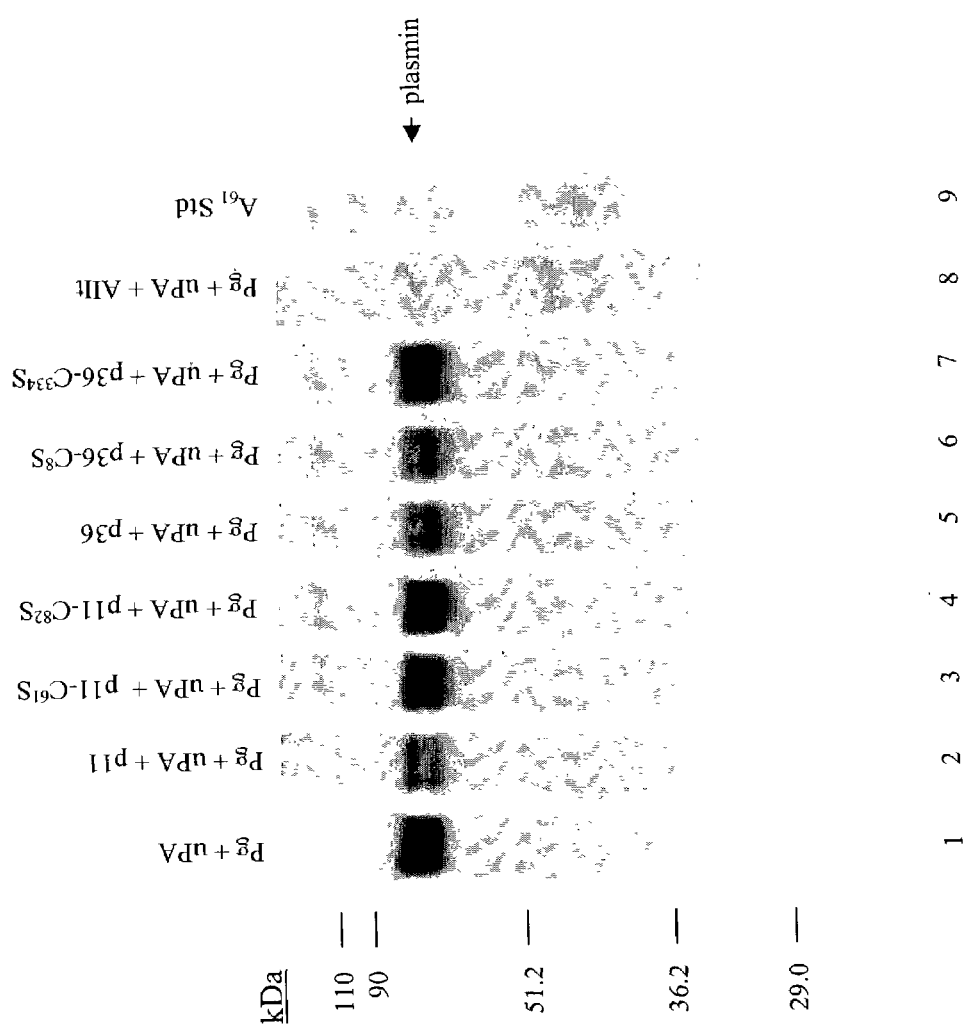
FIG. 2 Illustrates the role of p11 and p36 subunits in the plasmin reductase activity of AIIt. [Glu]-plasminogen (4 μM) was incubated with uPA (0.075 μM) and various subunits of AIIt or AIIt (4 μM). The results are shown as Coomassie blue staining (I) and Western blot with streptavidin-HRP (B).

AIIt is composed of two copies of a p36 polypeptide subunit and two copies of a p11 polypeptide subunit. As shown in FIGS. 2A,B the incubation of either the p36 or p11 subunit with u-PA and plasminogen stimulated the formation of $A_{61}$. However, AIIt appeared to be a more potent plasmin reductase than either subunit, suggesting that the interaction of the subunits potentiated the plasmin reductase activity of either subunit.

Figure 2B:
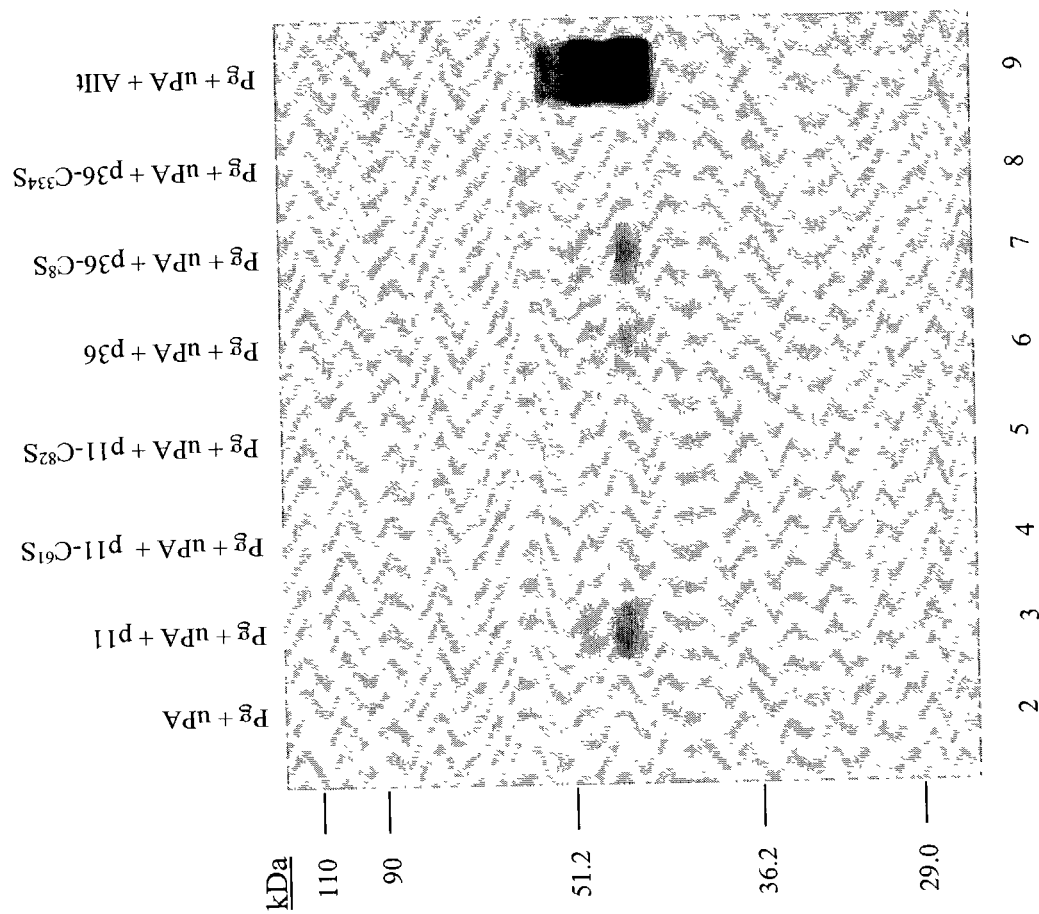

Theoretically, either the disulfides or cysteinyl residues of AIIt could participate in the reduction of plasmin. It is possible that upon plasminogen binding the disulfide of annexin II is reduced by the thiols of annexin II and the newly formed thiols participate in reduction of plasmin. Since the p11 subunit does not contain disulfides, it is reasonable to suspect that the thiols of this subunit were important for its plasmin reductase activity. p11 contains two cysteinyl residues: $Cys^{61}$ which plays a critical role in the binding of p36 and $Cys^{82}$ which is a free thiol (25). Two recombinant forms of this subunit were prepared, in which individual cysteinyl residues were mutated to serine. This conservative mutation results in the substitution of a thiol group for a hydroxyl group. As shown in FIG. 2B, substitution of either of these cysteine residues resulted in a loss of plasmin reductase activity of the p11 subunit. This suggests that both cysteinyl residues of p11 are required to sustain the plasmin reductase activity of the protein.

Human p36 contains two thiol-containing cysteines, $Cys^8$ and $Cys^{334}$. As shown in FIG. 2B, substitution of $Cys^{334}$, but not $Cys^8$, with serine blocked the plasmin reductase activity of p36. This result suggests that the $Cys^{334}$ thiol is critical for plasmin reductase activity of the p36 subunit.

Figure 3B:
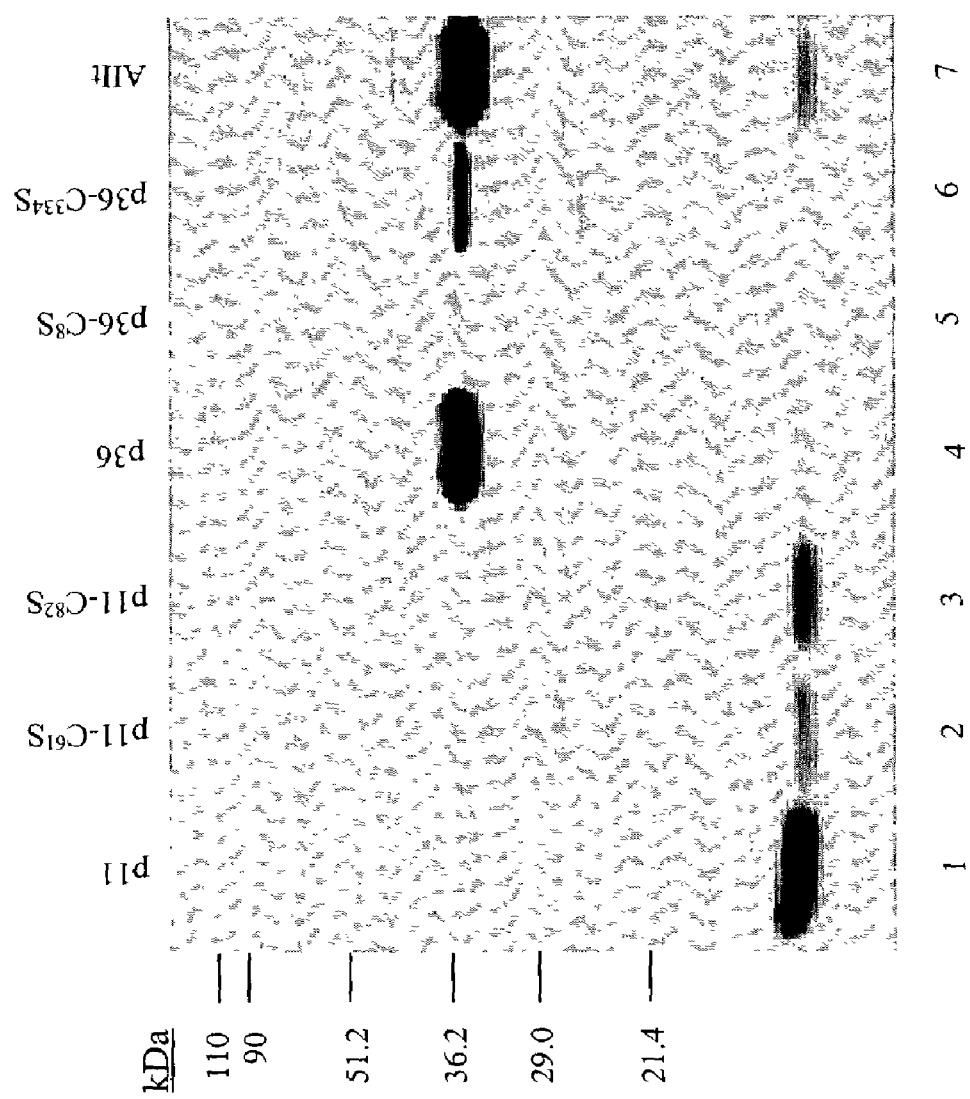
FIG. 3 illustrates the thiol reactivity of AIIt and its subunits. AIIt or its various subunits (2 μM) were incubated with MPB (100 μM), reduced glutathione and iodoacetamide, sequentially. The reaction mixtures were subjected to reduced SDS-PAGE followed by either Coomassie blue staining (A) or Western blot with streptavidin-HRP (B). (C) AIIt (18 μM) was incubated with iodoacetic acid (IAA, 10 mM) or MPB (200 μM). [Glu]-plasminogen (4 μM) was incubated with u-PA (0.075 μM) and the indicated AIIt (4 μM). The result shown is a Western blot with streptavidin-HRP.

To identify the reactive thiols of AIIt and its subunits, AIIt, p36 and p11 were incubated with MPB and resolved with SDS-PAGE followed by Coomassie blue staining (FIG. 3A) or Western blot with streptavidin-HRP (FIG. 3B). As shown in FIG. 3B, the p11 subunit and both $Cys^{61}Ser$ and $Cys^{82}Ser$ p11 mutants were labeled with MPB. In contrast, although p36 and the $Cys^{334}Ser$ p36 mutant were labeled with MPB, the $Cys^8Ser$ mutant was not labeled. This suggests that the thiols of the isolated p11 are accessible to MPB whereas the $Cys^{334}$ of p36 is not accessible. Interestingly, both the p36 and p11 subunits within AIIt were labeled with MPB. However, preincubation of AIIt with iodoacetic acid or MPB resulted in only a small decrease in the plasmin reductase activity of AIIt (FIG. 3C). This suggests that the $Cys^{334}$ thiol of the p36 subunit of AIIt is inaccessible to the solvent.

Since the $Cys^{334}$ residue is highly conserved among many of the annexins, seven other annexins were examined for plasmin reductase activity. As shown in FIG. 4, only annexin II p36 subunit and AIIt possessed plasmin reductase activity. This result establishes that plasmin reductase activity is not a common feature of the annexins.

Figure 5:
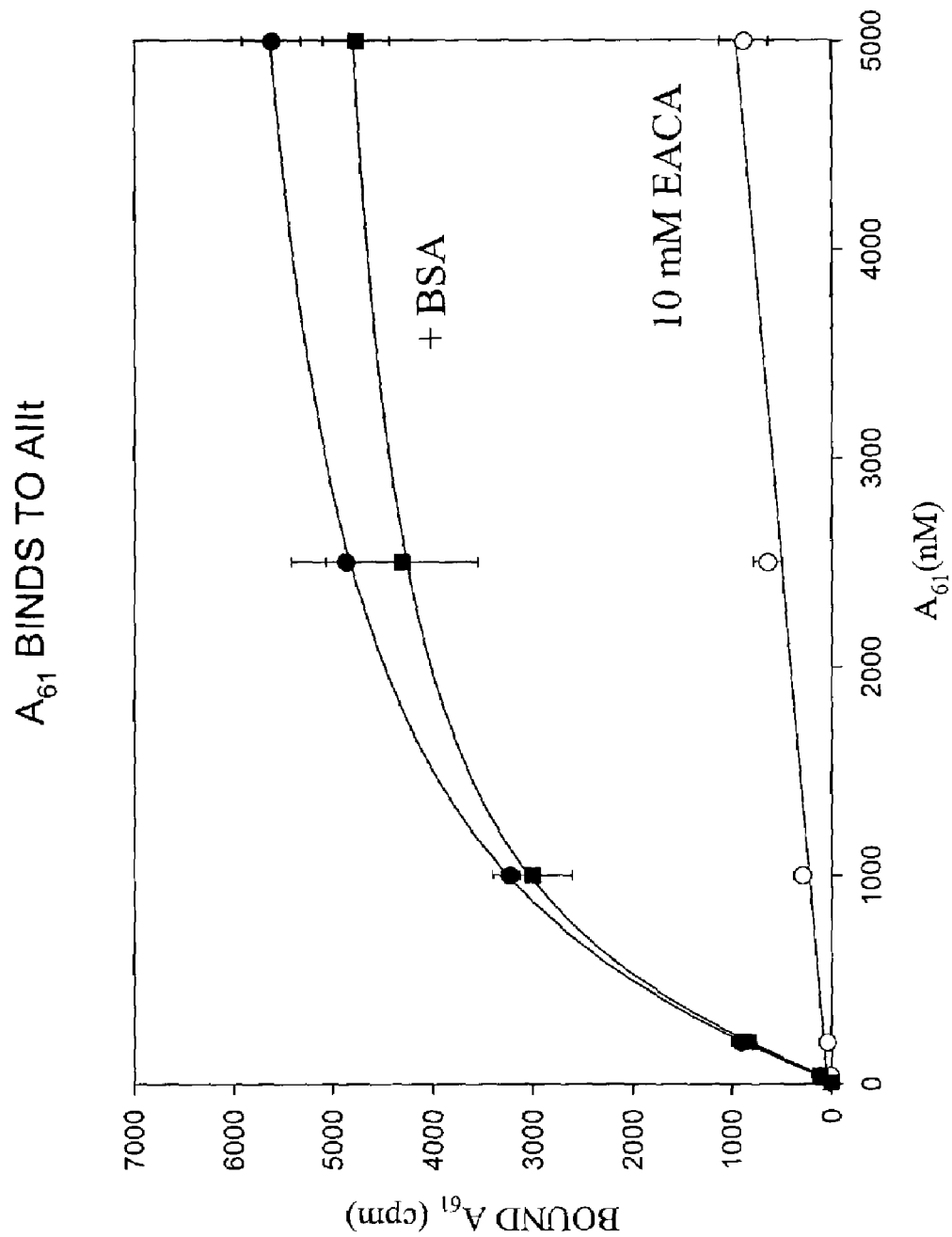
FIG. 5 illustrates the binding of $A_{61}$ to AIIt. The wells of Removawell™ strips were coated with phospholipid, blocked with bovine serum albumin, incubated with AIIt, and extensively washed. Various concentrations of iodinated $A_{61}$ were added into the AIIt-coated wells in the absence filled circles) or presence of 30-fold molar excess of bovine serum albumin (filled triangles) or cold $A_{61}$ (open circles). Individual wells were detached and measured for radioactivity with y-counter. The data shown (n=6) were the average of two separate experiments.

It is generally accepted in the art that AIIt binds both plasminogen and plasmin and is present at discrete regions of the extracellular surface (17;20;26). This suggested that AIIt could act as a scaffolding protein and focus the proteolytic activity of plasmin to the plasma membrane. It was unclear if the $A_{61}$ generated by cells could remain bound to AIIt at the cell surface or be immediately released into the media. However, as shown in FIG. 5, $A_{61}$ bound to AIIt with a $k_d$ of $1.0\pm0.05$ μM (n=6). According to the observation made by the inventors that $A_{61}$ did not block the stimulation of tPA-catalyzed conversion of plasminogen to plasmin, one skilled in the art may reasonably expect that the binding sites on AIIt for $A_{61}$ are distinct from those for plasminogen or plasmin. This suggests that some of the $A_{61}$ produced by the AIIt's plasmin reductase reaction may remain bound to AIIt at the cell surface.

EXAMPLE 2

Stimulation of $A_{61}$ Production by Other Disulfide Reductases

Figure 6:
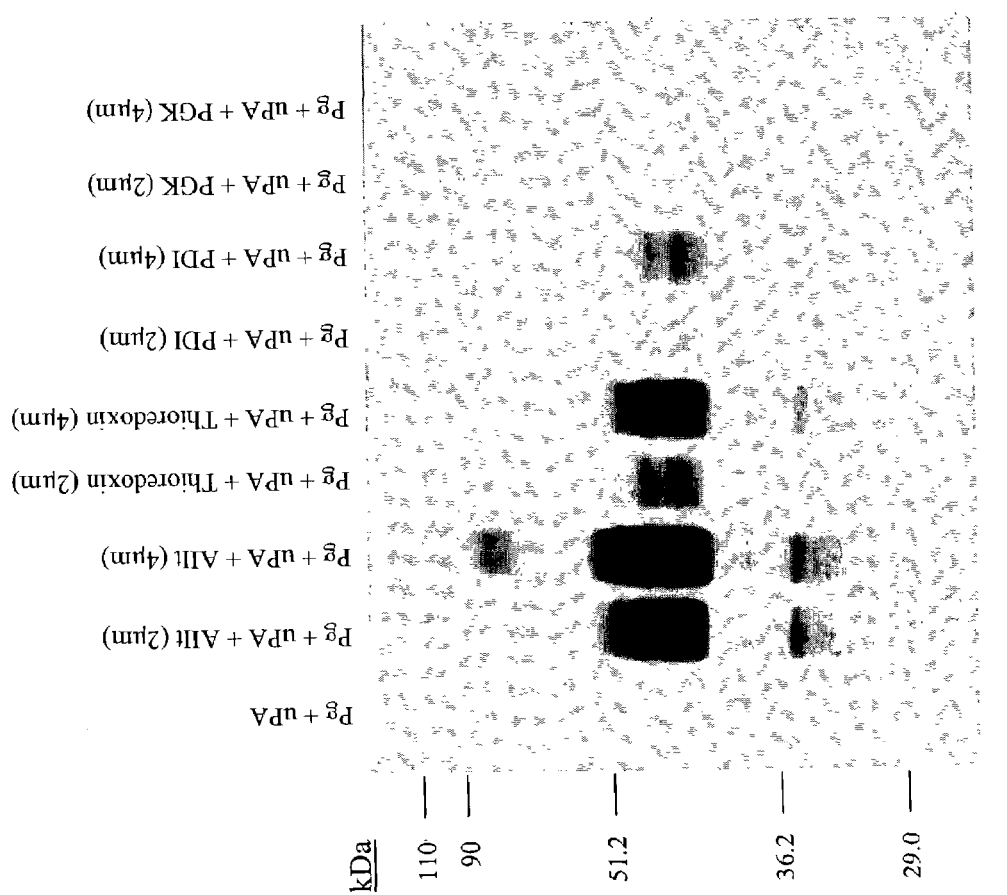
FIG. 6 illustrates a comparison of AIIt with other disulfide reductases. [Glu]-plasminogen (4 μM) was incubated with uPA (0.075 FM) and the various proteins as indicated. The result shown is a Western blot with streptavidin-HRP.

Protein disulfide isomerase, thioredoxin and phosphoglycerate kinase are three protein disulfide reductases that are secreted by cultured cells (16;27-29). The three reductases have been shown to act as plasmin reductases (15;16). As shown in FIG. 6, under the assay conditions AIIt was a more potent plasmin reductase than the other reductases in vitro.

Thioredoxin and protein disulfide isomerase share a common sequence, Trp-Cys-Gly-Pro-Cys-Lys (SEQ ID NO:4), which participates in the cleavage, formation and reshuffling of disulfide bonds. This sequence is not present in phosphoglycerate kinase or AIIt, suggesting that these reductases have distinct catalytic mechanisms. Typically, the disulfide reductase activity of thioredoxin or protein disulfide isomerase is measured by determination of their rates of reduction of insulin disulfide (30;31). Interestingly, although protein disulfide isomerase and thioredoxin exhibit potent insulin reductase activity, AIIt failed to exhibit insulin reductase activity. This further confirms that the catalytic mechanism of AIIt is distinct from that of some other protein reductases.

EXAMPLE 3

Down-Regulation of AIIT Blocks $A_{61}$, Generation

Figure 7A:
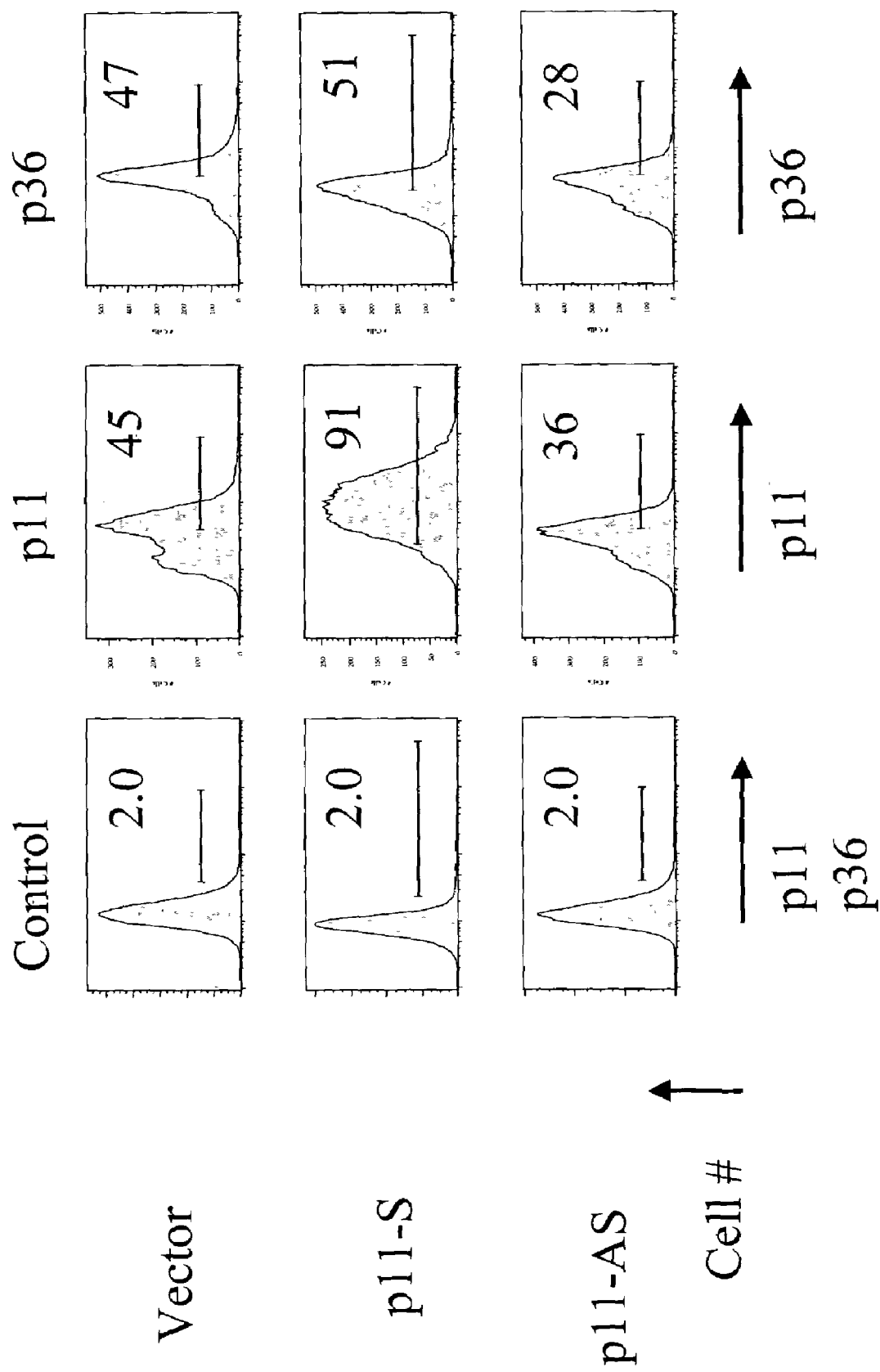
FIG. 7 illustrates that the down-regulation of AIIt blocks A, generation by HT1080 cells. (A) Flow cytometric analysis of transduced HT1080 cells. (B,C) Comparison of the generation of $A_{61}$ by transduced HT1080 cells. Transduced HT1080 cells were incubated with DMEM containing 2 μM [Glu]-plasminogen (B) or plasmin (C). After the indicated time of incubation, the medium was analyzed by reduced SDS-PAGE (B) or non-reduced SDS-PAGE (C) followed by Western blot with monoclonal anti-human plasminogen kringle 1-3 antibody.
Figure 7B:
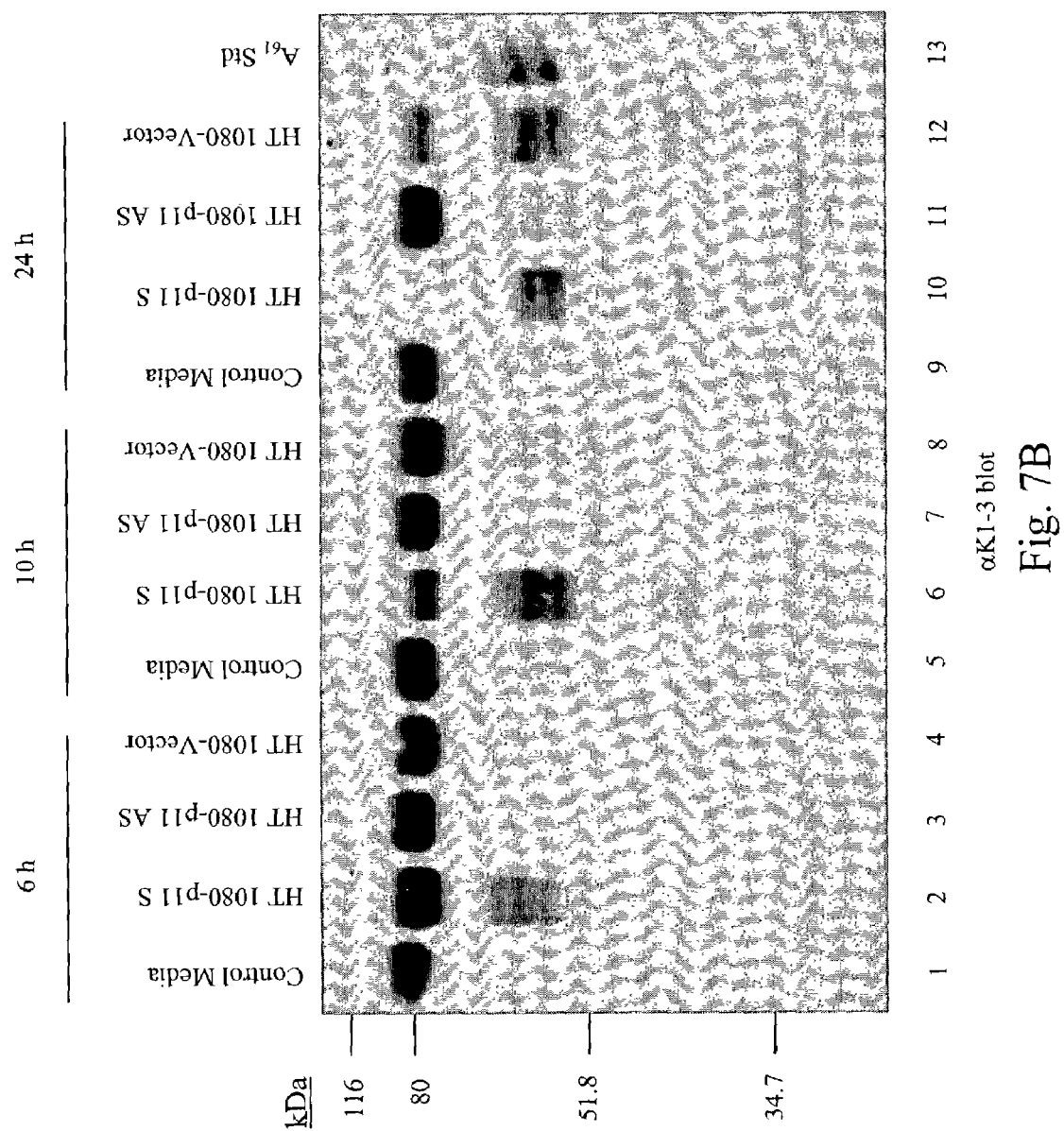

HT1080 fibrosarcoma cells were stably transfected (transduced) with a pLin retroviral vector encoding a p11 gene in the sense (pLin-p11S) or antisense (pLin-p11AS) orientation, or an empty pLin vector (pLin-V). The pLin-p11AS transduced cells showed a decrease in both p11 and p36 subunits on the cell surface whereas pLin-p1S transduced cells showed an increase in both p11 and p36 subunits (FIG. 7A). As shown in FIG. 7B, incubation of the pLin-p11S transduced cells with plasminogen resulted in enhanced $A_{61}$ formation compared to the pLin-V control cells. In contrast, the pLin-p11AS transduced cells failed to produce $A_{61}$. Additionally, HeLa cells transfected with a p11 antisense expressing vector also failed to convert plasminogen to $A_{61}$.

The data in FIG. 7B establishes a role for AIIt in $A_{61}$ formation in HT1080 fibrosarcoma cells. However, it is unclear if plasmin could be directly reduced or if plasmin autoproteolysis preceded plasmin reduction. As shown in FIG. 7C, the incubation of plasmin with the pLin-p11S cells also resulted in the accelerated disappearance of plasmin and concomitant enhanced appearance of $A_{61}$ compared with pLin-p11V cells. In contrast, the pLin-p11AS cells showed reduced plasmin loss and concomitant $A_{61}$ formation compared to the pLin-p11V cells. In another series of experiments, plasmin was inactivated by prior treatment of the serine protease inhibitor, DIFP and then incubated with the HT1080 cells. However, $A_{61}$ production by the cells was not observed. Furthermore, the catalytically inactive plasmin that was incubated with the cells was not reduced since it did not react with MPB. This result may be interpreted by the skilled artisan to mean that plasmin autoproteolysis is required before plasmin reduction can occur. Collectively, the experimental observations herein disclosed suggest that the mechanism of $A_{61}$ formation involves the u-PA-dependent conversion of plasminogen to plasmin followed by plasmin autoproteolysis and reduction of cleaved plasmin (FIG. 8).

EXAMPLE 4

Materials and Procedures Employed

Two-chain urokinase-type plasminogen activator (EPA) was a generous gift from Dr. H. Stack (Abbott Laboratories). [Glu]-plasminogen and plasmin were purchased from American Diagnostica. Antiangiogenic plasminogen fragment ($A_{61}$) was purified as outlined in copending patent application PCT/US01/44515. Annexin II heterotetramer (AIIt) and other annexins were purified from bovine lung as described in reference 21. Monoclonal anti-human plasminogen kringle 1-3 antibody was purchased from Enzyme Research Laboratories Inc. Monoclonal anti-annexin II and anti-annexin II fight chain antibodies were purchased from Transduction Laboratories. Anti-mouse horseradish peroxidase-conjugated secondary antibody was purchased from Santa Cruz Biotechnology. Horseradish peroxidase-conjugated streptavidin and protein disulfide isomerase were purchased from Calbiochem. Anti-mouse R-phycoerytbrin-conjugated secondary antibody was purchased from Caltag Laboratories Inc. $N^{\alpha}$-(3-maleimidylpropionyl)biocytin (MPB) was purchased from Molecular Probes. Reduced glutathione, iodoacetamide, lodoacetic acid, diisopropylfluorophosphate (DIFP), and thioredoxin were purchased from Sigma. L-lysine-Sepharose was purchased from Amersham Phannacia Biotech. lodobeads were purchased from Pierce. Phosphoglycerate kinase (PGK) was a generous gift from Dr. P. J. Hogg (Center for Thrombosis and Vascular Research, University of New South Wales, Sydney, Australia). Stably transfected HeLa cells expressing p11 antisense or sense mRNA were a generous gift from Dr. J. H. Shelhamer (Critical Care Medicine Department, National Institutes of Health, USA). HT1080 fibrosarcoma cells were obtained from American Type Culture Collection. Dulbecco's modified eagle medium (DMEM) was purchased from Life Technologies.

Mutagenesis of Annexin II and p11—Bacterial expression vectors containing the wild-type sequence for annexin II (pAED4.91-annexin II) and p11 (pAED4.91-p11) were mutated using the QuikChange™ Site-Directed Mutagenesis Kit (Stratagene). Briefly, mutagenic primers were synthesized that introduced Cys→Ser mutations at positions 8 and 334 of annexin II, as well as positions 61 and 82 of p11. All of the mutations introduced were verified by DNA sequence analysis. These various plasrids were then transformed into *E. coli* BL21 (DE3) and grown as previously described (22).

Purification of Wild-type and Mutant Annexin II—After 4 hours of induction with IPTG, bacteria were collected by low speed centrifugation. The cells were subsequently sonicated in lysis buffer (10 mM irmidazole, pH 7.5, 150 mM NaCl, 2 mM EGTA, 1 mM DTT+protease inhibitors) and centrifuged at 100,000×g for 1 hour at 4° C. Both mutant annexin II proteins were purified in the same manner as wild-type annexin II via hydroxyapatite, heparin-Sepharose affinity and gel penneation chromatography as reported previously (22). The elution profiles of the recombinant wild-type and mutant annexin II on hydroxyapatite, heparin affinity and gel permeation chromatography were indistinguishable. In addition, the circular dichroism spectra of each of the proteins were very similar, indicating little secondary structure perturbation.

Purification of Wild-type and Mutant p11—After 4 hours of induction with IPTG, bacteria were collected by low speed centrifugation. The cells were subsequently sonicated in lysis buffer (100 mM Tris-HCl, pH 7.5, 200 mM NaCl, 10 mM $MgCl_2$, 2 mM DTT+protease inhibitors) and centrifuged at 100,000×g for 1 h at 4° C. Both p11 mutants were purified in the same manner as wild-type p11 (23). Briefly, the cell lysis supematant was precipitated with 50% $(NH_4)_2SO_4$, and the supernatant was applied to a Butyl-Sepharose column equilibrated in lysis buffer containing 50% $(NH_4)2SO_4$. The p11 was eluted with a linear gradient of $(NH_4)_2SO_4$ from 50% to 0%, and peak fractions containing p11 were pooled and dialyzed against 10 mM imidazole, pH 7.4, 1 mM EGTA, 0.5 mM DTT, and 0.1 mM EDTA. The dialyzed fractions were subsequently applied to a DEAE-Sepharose column equilibrated in the same buffer. The p11 was eluted with a linear NaCl gradient, concentrated to 4 mL, and applied to a Sephacryl S-100 column equilibrated in 40 mM Tris-HCl, pH 7.4, 0.1 mM EGTA, and 0.1 mM DTT. A single protein peak was recovered at the expected molecular weight based on gel filtration standards.

Plasmid Construction and Transfection of HT1080 Cells—Sense and antisense p11 expression vector were produced by cloning the full-length human p11 cDNA into the pLin retroviral vector in the sense (pLin-p11S) or antisense orientation (pLin-p11AS) as reported (24). Control cells transduced with the vector alone (pLin-V) were also established. The pLin vector carries the Moloney murine leukemia virus 5' LTR enhancer/promoter region to promote strong, constitutive expression of the cloned p11 inserts and neomycin phosphotransferase gene in mammalian cells. The pLin constructs were propagated in a PA317 retroviral packaging cell line. Packaging cells were selected in 300 µg/ml neomycin and conditioned media that contained high titers of the virus were used to transduce the HT1080 fibrosarcoma cells. After viral transduction the neomycin resistant HT1080 fibrosarcoma cells were cloned and permanent cell lines established (Choi, K-S et al., in press at FASB J.).

Dialysis of Candidate Plasmin Reductase Proteins—After purification or reconstitution, AIIt, p11, p36 (annexin II), other annexins, thioredoxin, protein disulfide isomerase, and phosphoglycerate kinase were dialyzed against 20 mM Tris (pH 7.5) and 140 mM NaCl under argon gas to prevent possible oxidation.

Plasmin Reductase Assay—[Glu]-plasminogen (4 µM) was incubated with 0.075 µM u-PA and a candidate plasmin reductase protein (4 µM, unless described) in a buffer containing 20 mM Tris (pH 7.5) and 140 mM NaCl at 37° C. for 2 h. A portion of reaction mixture was diluted with SDS-PAGE sample buffer and subjected to non-reduced SDS-PAGE followed by Coomassie blue staining. To label any free thiol groups of produced protein(s), the reaction mixture was incubated with 100 µM MPB at room temperature for 30 min. The reaction mixture was then treated with 200 µM reduced glutathione at room temperature for 10 min to quench the unreacted MPB. The unreacted glutathione and other free thiols in the reaction mixture were blocked with 400 µM of iodoacetamide at room temperature for 10 min. Then the reaction mixture was incubated with L-lysine-Sepharose at room temperature for 30 min to purify the kringle-containing, plasminogenderived proteins. The matrix was extensively washed with PBS and the bound proteins were eluted by boiling the resin with SDS-PAGE sample buffer. Each sample was subjected to non-reduced SDS-PAGE followed by Western blot with horseradish peroxidase-conjugated streptavidin (streptavidin-HRP) as indicated below.

Detection offree thiols in AIIt—2 µM AIIt, p11, or p36 was incubated with 100 µM MPB in a buffer containing 20 mM Tris (pH 7.5) and 140 mM NaCl at room temperature for 30 min. After incubation, 200 µM reduced glutathione and 400 µM iodoacetamide were added sequentially, and the reaction mixture was subjected to reduced SDS-PAGE followed by either Coomassie blue staining or Western blot with streptavidin-HRP as indicated below.

Cell-Mediated Generation of $A_{61}$—Transduced HT1080 cells were maintained in DMEM supplemented with 10% heat-inactivated fetal bovine serum, 2 mM L-glutamine, 10 units/ml penicillin G, 10 µM streptomycin sulfate, and 300 µg/ml neomycin. Approximately $1 \times 10^5$ cells were added to each well of 24-well tissue culture plates and incubated at 37° C. for 24 h. The cell monolayers were then washed three times with DMEM and 2 µM [Glu]-plasminogen, plasmin, or diisopropylfluorophosphate (DIFP)-treated plasmin in DMEM was added to each well. The conditioned medium was removed at indicated times, diluted with SDS-PAGE sample buffer with or without β-mercaptoethanol and subjected to SDS-PAGE followed by Western blot with monoclonal anti-human plasminogen kringle 1-3 antibody (anti-K1-3) as indicated below.

Electrophoresis and Western Blot—Samples were diluted with SDS-PAGE sample buffer and subjected to SDS-PAGE and electrophoretically transferred to nitrocellulose membrane (0.45 µm pore size) at 4° C. for 1 h. The membrane was blocked in TPBS (phosphate buffered saline containing 0.1% Tween-20) with 5% skim milk at room temperature for 1 h and incubated at 4° C. overnight with a 0.4 µg/mnl monoclonal antihuman plasminogen ktingle 1-3 antibody in TPBS with 5% skim milk. The blot was extensively washed with TPBS at room temperature and then incubated at room temperature for 1 h with a 0.16 µg/ml horseradish peroxidase-conjugated goat anti-mouse secondary antibody in TPBS with 5% skim milk. In the case of MPB-reacted protein samples, the membrane was blocked and incubated at room temperature for 1 h with a 0.1 µg/ml streptavidin-HRP in TPBS with 5% skim milk. The membrane was extensively washed with TPBS and visualized by enhanced chemiluminescence (Pierce).

Binding of $A_{61}$ to AIIt—The purified $A_{61}$ was iodinated according to manufacturer's procedures. Iodinated $A_{61}$ retained biological activity as determined by the endothelial cell proliferation assay (14). 96-well Immulon-1 Removawell strips (Dynex Technologies) were coated with phospholipid mixture containing 3:1 ratio of phosphatidylserine to phosphatidylcholine and air-dried. The coated strips were blocked with 1% fatty acid-free bovine serum albumin (BSA) in a buffer containing 20 mM Hepes (pH 7.4), 140 mM NaCl, and 2 mM $CaCl_2$ (buffer A) at room temperature for 2 h. The strips were washed with buffer A and incubated with 1 µM AIIt in buffer A at room temperature for 4 h. The strips were then washed and incubated with 0.008-5 µM iodinated $A_{61}$ with or without 30-fold molar excess of cold $A_{61}$ or BSA at 4° C. After overnight incubation, the strips were washed five times with PBS, and individual wells were detached and measured for radioactivity with a γ-counter. The data shown (n=6) are the average of two separate experiments.

Flow Cytometric Analysis of Transduced HT 1080 Cells—Transduced HT 1080 cells were harvested and $1 \times 10^6$ cells in PBS were divided into each tube. The cells were fixed with 4% paraformaldehyde in PBS at room temperature for 20 min and washed twice with PBS. The cells were then incubated with 1 µg of monoclonal anti-annexin II or anti-annexin II light chain antibody at room temperature for 30 min. For the control staining, 1 µg of mouse Ig G was used. The cells were washed and incubated with 2 µg/ml anti-mouse R-phycoerythrin-conjugated secondary antibody at room temperature for 30 min. The cells were washed and subjected to flow cytometric analysis using FACScan™ (Beckton Dickinson) and analyzed by the FlowJo™ program. The data shown are a representative of three separate experiments.

As various changes could be made in the above methods and compositions without departing from the scope of the invention, it is intended that all matter contained in the above description and sequence listing, and shown in the accompanying drawings shall be interpreted as illustrative and not in a limiting sense.

All references cited in this specification are hereby incorporated by reference. The discussion of references herein is intended merely to summarize the assertions made by their authors and no admission is made that any reference constitutes prior art. Applicants reserve the right to challenge the accuracy and pertinence of the cited references.

---

What is claimed is:

1. A method of producing an anti-angiogenic $A_{61}$ plasmin fragment consisting of the amino acid sequence of SEQ ID NO:7 or SEQ ID NO:8, the method comprising contacting a plasmin polypeptide with annexin II heterotetramer, annexin II p36 subunit, or annexin II p11 subunit, wherein a reduced plasmin protein is produced and the anti-angiogenic $A_{61}$ plasmin fragment is released from the reduced plasmin protein.

2. The method of claim 1 wherein the annexin II heterotetramer subunit is annexin II p36 subunit.

3. The method of claim 1 wherein the annexin II heterotetramer subunit is annexin II p11 subunit.

4. The method of claim 1 wherein the annexin II heterotetramer is associated with a cell membrane.

5. A method of producing an $A_{61}$ anti-angiogenesis plasmin fragment consisting of the amino acid sequence of SEQ ID NO:7 or SEQ ID NO:8, the method comprising contacting a plasminogen polypeptide with a urokinase-type plasminogen activator and an annexin II heterotetramer, wherein a reduced plasmin protein is produced and the $A_{61}$ anti-angiogenesis plasmin fragment, which has anti-angiogenesis activity, is released from the reduced plasmin protein.

6. The method of claim 5 wherein the annexin II heterotetramer is associated with a cell membrane.

* * * * *

UNITED STATES PATENT AND TRADEMARK OFFICE
CERTIFICATE OF CORRECTION

PATENT NO. : 7,250,271 B2
APPLICATION NO. : 10/304287
DATED : July 31, 2007
INVENTOR(S) : David Waisman and Mijung Kwan It is certified that error appears in the above-identified patent and that said Letters Patent is hereby corrected as shown below:

Col. 2, Line 31 "4790-"; should be -- 4790-4799 --.
Col. 2, Line 41 "Heiwig"; should be -- Helwig --.
Col. 2, Line 55 "Wolhman"; should be -- Wollman --.
Col. 3, Line 30 "antangiogenic"; should be -- anti-angiogenic --.
Col. 3, Line 33 "mnacrophages"; should be -- macrophages --.
Col. 3, Line 61 "sulthydryl"; should be -- sulfhydryl --.
Col. 4, Line 4 "A,"; should be -- $A_{61}$ --.
Col. 4, Line 15 "Al"; should be -- $A_{61}$ --.
Col. 4, Line 66 "requited"; should be -- required --.
Col. 5, Line 14 ""plasrrinogen"; should be -- plasminogen --.
Col. 5, Line 30 "(I)"; should be -- (A) --.
Col. 5, Line 53 "filled"; should be -- (filled --.
Col. 5, Line 56 "y-counter"; should be --γ-counter --.
Col. 5, Line 60 "(0.075 FM)"; should be -- (0.075 μM) --.
Col. 5, Line 63 "A,"; should be -- A61 --.
Col. 6, Line 9 "Lys469"; should be -- Lys468 --
Col. 6, Line 28 "FIG. 8)."; should be -- (FIG. 8). --.
Col. 6, Line 28 "Arg561"; should be -- Arg561 --.
Col. 6, Line 36 "$Cys^{54}1$"; should be -- $Cys^{541}$ --.
Col. 8, Line 35 "A1"; should be -- $A_{61}$ --.
Col. 8, Line 39 "3-(N-raleidylpropionyl)biocytin"; should be
-- 3-(N-maleimidylpropionyl)biocytin --.
Col. 8, Line 49 "A6,"; should be -- $A_{61}$ --.
Col. 10, Line 37 "pLin-p1S" should be -- pLin-p11S --.
Col. 11, Line 5 "(EPA)"; should be -- (u-PA) --.
Col. 11, Line 15 "fight"; should be -- light --.
Col. 11, Line 24 "Iodoacetic"; should be -- iodoacetic --.
Col. 11, Line 27 "Phannacia"; should be -- Pharmacia --.
Col. 11, Line 27 "Iodobeads"; should be --Iodobeads --.
Col. 11, Line 46 "plasrids"; should be -- plasmids --.
Col. 11, Line 52 "irmidazole"; should be -- imidazole --.
Col. 11, Line 57 "penneation"; should be -- permeation --.
Col. 12, Line 4 "supematant"; should be -- supernatant --.
Col. 12, Line 58 "plasminogenderived"; should be -- plasminogen-derived --.
Col. 12, Line 65 "offree"; should be -- of free --.
Col. 13, Line 27 "/mnl"; should be -- /ml --.
Col. 13, Line 28 "antihuman"; should be -- anti-human --.

UNITED STATES PATENT AND TRADEMARK OFFICE
CERTIFICATE OF CORRECTION

PATENT NO.        : 7,250,271 B2
APPLICATION NO.   : 10/304287
DATED             : July 31, 2007
INVENTOR(S)       : David Waisman and Mijung Kwan It is certified that error appears in the above-identified patent and that said Letters Patent is hereby corrected as shown below:

Col. 13, Line 28 "ktingle"; should be -- kringle --.

Signed and Sealed this

Sixth Day of November, 2007

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 791
<212> TYPE: PRT
<213> ORGANISM: mammalian

<400> SEQUENCE: 1

Glu Pro Leu Asp Asp Tyr Val Asn Thr Gln Gly Ala Ser Leu Phe Ser
 1               5                  10                  15

Val Thr Lys Lys Gln Leu Gly Ala Gly Ser Ile Glu Glu Cys Ala Ala
                20                  25                  30

Lys Cys Glu Glu Asp Glu Glu Phe Thr Cys Arg Ala Phe Gln Tyr His
            35                  40                  45

Ser Lys Glu Gln Gln Cys Val Ile Met Ala Glu Asn Arg Lys Ser Ser
        50                  55                  60

Ile Ile Ile Arg Met Arg Asp Val Val Leu Phe Glu Lys Lys Val Tyr
```

-continued

```
             65                  70                  75                  80
Leu Ser Glu Cys Lys Thr Gly Asn Gly Lys Asn Tyr Arg Gly Thr Met
                         85                  90                  95
Ser Lys Thr Lys Asn Gly Ile Thr Cys Gln Lys Trp Ser Ser Thr Ser
             100                 105                 110
Pro His Arg Pro Arg Phe Ser Pro Ala Thr His Pro Ser Glu Gly Leu
             115                 120                 125
Glu Glu Asn Tyr Cys Arg Asn Pro Asp Asn Asp Pro Gln Gly Pro Trp
             130                 135                 140
Cys Tyr Thr Thr Asp Pro Glu Lys Arg Tyr Asp Tyr Cys Asp Ile Leu
145                 150                 155                 160
Glu Cys Glu Glu Glu Cys Met His Cys Ser Gly Glu Asn Tyr Asp Gly
                         165                 170                 175
Lys Ile Ser Lys Thr Met Ser Gly Leu Glu Cys Gln Ala Trp Asp Ser
             180                 185                 190
Gln Ser Pro His Ala His Gly Tyr Ile Pro Ser Lys Phe Pro Asn Lys
             195                 200                 205
Asn Leu Lys Lys Asn Tyr Cys Arg Asn Pro Asp Arg Glu Leu Arg Pro
             210                 215                 220
Trp Cys Phe Thr Thr Asp Pro Asn Lys Arg Trp Glu Leu Cys Asp Ile
225                 230                 235                 240
Pro Arg Cys Thr Thr Pro Pro Ser Ser Gly Pro Thr Tyr Gln Cys
                         245                 250                 255
Leu Lys Gly Thr Gly Glu Asn Tyr Arg Gly Asn Val Ala Val Thr Val
             260                 265                 270
Ser Gly His Thr Cys Gln His Trp Ser Ala Gln Thr Pro His Thr His
             275                 280                 285
Asn Arg Thr Pro Glu Asn Phe Pro Cys Lys Asn Leu Asp Glu Asn Tyr
             290                 295                 300
Cys Arg Asn Pro Asp Gly Lys Arg Ala Pro Trp Cys His Thr Thr Asn
305                 310                 315                 320
Ser Gln Val Arg Trp Glu Tyr Cys Lys Ile Pro Ser Cys Asp Ser Ser
                         325                 330                 335
Pro Val Ser Thr Glu Gln Leu Ala Pro Thr Ala Pro Pro Glu Leu Thr
             340                 345                 350
Pro Val Val Gln Asp Cys Tyr His Gly Asp Gly Gln Ser Tyr Arg Gly
             355                 360                 365
Thr Ser Ser Thr Thr Thr Thr Gly Lys Lys Cys Gln Ser Trp Ser Ser
             370                 375                 380
Met Thr Pro His Arg His Gln Lys Thr Pro Glu Asn Tyr Pro Asn Ala
385                 390                 395                 400
Gly Leu Thr Met Asn Tyr Cys Arg Asn Pro Asp Ala Asp Lys Gly Pro
                         405                 410                 415
Trp Cys Phe Thr Thr Asp Pro Ser Val Arg Trp Glu Tyr Cys Asn Leu
             420                 425                 430
Lys Lys Cys Ser Gly Thr Glu Ala Ser Val Val Ala Pro Pro Pro Val
             435                 440                 445
Val Leu Leu Pro Asp Val Glu Thr Pro Ser Glu Glu Asp Cys Met Phe
             450                 455                 460
Gly Asn Gly Lys Gly Tyr Arg Gly Lys Arg Ala Thr Thr Val Thr Gly
465                 470                 475                 480
Thr Pro Cys Gln Asp Trp Ala Ala Gln Glu Pro His Arg His Ser Ile
                         485                 490                 495
```

```
Phe Thr Pro Glu Thr Asn Pro Arg Ala Gly Leu Glu Lys Asn Tyr Cys
            500                 505                 510

Arg Asn Pro Asp Gly Asp Val Gly Pro Trp Cys Tyr Thr Thr Asn
        515                 520                 525

Pro Arg Lys Leu Tyr Asp Tyr Cys Asp Val Pro Gln Cys Ala Ala Pro
        530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
        610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
        770                 775                 780

Glu Gly Val Met Arg Asn Asn
785                 790

<210> SEQ ID NO 2
<211> LENGTH: 319
<212> TYPE: PRT
<213> ORGANISM: mammalian

<400> SEQUENCE: 2

Met Ser Thr Val His Glu Ile Leu Cys Lys Leu Ser Leu Glu Gly Asp
 1               5                  10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
```

```
            65                  70                  75                  80
Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
            115                 120                 125

Ile Glu Ile Ile Cys Ser Arg Thr Asn Gln Glu Leu Gln Glu Ile Asn
        130                 135                 140

Arg Val Tyr Lys Glu Met Tyr Lys Thr Asp Leu Glu Lys Asp Ile Ile
145                 150                 155                 160

Glu Asp Gly Ser Val Ile Asp Tyr Glu Leu Ile Asp Gln Asp Ala Arg
                165                 170                 175

Asp Leu Tyr Asp Ala Gly Val Lys Arg Lys Gly Thr Asp Val Pro Lys
                180                 185                 190

Trp Ile Ser Ile Met Thr Glu Arg Ser Val Pro His Leu Gln Lys Val
            195                 200                 205

Phe Asp Arg Tyr Lys Ser Tyr Ser Pro Tyr Asp Met Leu Glu Ser Ile
        210                 215                 220

Arg Lys Glu Val Lys Gly Asp Leu Glu Asn Ala Phe Leu Asn Leu Val
225                 230                 235                 240

Gln Cys Ile Gln Asn Lys Pro Leu Tyr Phe Ala Asp Arg Leu Tyr Asp
                245                 250                 255

Ser Met Lys Gly Lys Gly Thr Arg Asp Lys Val Leu Ile Arg Ile Met
                260                 265                 270

Val Ser Arg Ser Glu Val Asp Met Leu Lys Ile Arg Ser Glu Phe Lys
            275                 280                 285

Arg Lys Tyr Gly Lys Ser Leu Tyr Tyr Tyr Ile Gln Gln Asp Thr Lys
        290                 295                 300

Gly Asp Tyr Gln Lys Ala Leu Leu Tyr Leu Cys Gly Gly Asp Asp
305                 310                 315

<210> SEQ ID NO 3
<211> LENGTH: 97
<212> TYPE: PRT
<213> ORGANISM: mammalian

<400> SEQUENCE: 3

Met Pro Ser Gln Met Glu His Ala Met Glu Thr Met Met Phe Thr Phe
  1               5                  10                  15

His Lys Phe Ala Gly Asp Lys Gly Tyr Leu Thr Lys Glu Asp Leu Arg
            20                  25                  30

Val Leu Met Glu Lys Glu Phe Pro Gly Phe Leu Glu Asn Gln Lys Asp
        35                  40                  45

Pro Leu Ala Val Asp Lys Ile Met Lys Asp Leu Asp Gln Cys Arg Asp
    50                  55                  60

Gly Lys Val Gly Phe Gln Ser Phe Phe Ser Leu Ile Ala Gly Leu Thr
65                  70                  75                  80

Ile Ala Cys Asn Asp Tyr Phe Val Val His Met Lys Gln Lys Gly Lys
                85                  90                  95

Lys
97

<210> SEQ ID NO 4
<211> LENGTH: 6
```

```
<212> TYPE: PRT
<213> ORGANISM: mammalian

<400> SEQUENCE: 4

Trp Cys Gly Pro Cys Lys
 1               5

<210> SEQ ID NO 5
<211> LENGTH: 291
<212> TYPE: DNA
<213> ORGANISM: mammalian

<400> SEQUENCE: 5
cttctttccc ttctgcttca tgtgtactac aaaatagtca ttgcatgcaa tggtgaggcc      60
cgcaattagg gaaaagaagc tctggaagcc cactttgcca tctctacact ggtccaggtc     120
cttcattatt ttgtccacag ccagagggtc ttttttgattt ccaaaaatc cagggaactc     180 cttttccatg agtactctca ggtcctcctt tgttaagtag cctttatccc cagcgaattt     240
gtgaaatgta acatcatgg tttccatggc gtgttccatt tgagatggca t               291

<210> SEQ ID NO 6
<211> LENGTH: 291
<212> TYPE: DNA
<213> ORGANISM: mammalian

<400> SEQUENCE: 6
atgccatctc aaatggaaca cgccatggaa accatgatgt ttacatttca caaattcgct      60
ggggataaag gctacttaac aaaggaggac ctgagagtac tcatggaaaa ggagttccct     120
ggatttttgg aaaatcaaaa agaccctctg gctgtggaca aataatgaa ggacctggac      180 cagtgtagag atggcaaagt gggcttccag agcttctttt ccctaattgc gggcctcacc     240
attgcatgca atgactattt tgtagtacac atgaagcaga agggaaagaa g              291

<210> SEQ ID NO 7
<211> LENGTH: 391
<212> TYPE: PRT
<213> ORGANISM: mammalian

<400> SEQUENCE: 7

Lys Val Tyr Leu Ser Glu Cys Lys Thr Gly Asn Gly Lys Asn Tyr Arg
 1               5                  10                  15

Gly Thr Met Ser Lys Thr Lys Asn Gly Ile Thr Cys Gln Lys Trp Ser
                20                  25                  30

Ser Thr Ser Pro His Arg Pro Arg Phe Ser Pro Ala Thr His Pro Ser
            35                  40                  45

Glu Gly Leu Glu Glu Asn Tyr Cys Arg Asn Pro Asp Asn Asp Pro Gln
        50                  55                  60

Gly Pro Trp Cys Tyr Thr Thr Asp Pro Glu Lys Arg Tyr Asp Tyr Cys
 65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140
```

-continued

```
Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
                260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Thr Gly Lys Lys Cys Gln Ser
        290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
                340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
        370                 375                 380

Cys Met Phe Gly Asn Gly Lys
385                 390

<210> SEQ ID NO 8
<211> LENGTH: 394
<212> TYPE: PRT
<213> ORGANISM: mammalian

<400> SEQUENCE: 8

Lys Val Tyr Leu Ser Glu Cys Lys Thr Gly Asn Gly Lys Asn Tyr Arg
 1               5                  10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125
```

```
Pro Asn Lys Asn Leu Lys Lys Asn Tyr Cys Arg Asn Pro Asp Arg Glu
        130             135             140

Leu Arg Pro Trp Cys Phe Thr Thr Asp Pro Asn Lys Arg Trp Glu Leu
145             150             155                         160

Cys Asp Ile Pro Arg Cys Thr Thr Pro Pro Ser Ser Gly Pro Thr
                165             170             175

Tyr Gln Cys Leu Lys Gly Thr Gly Glu Asn Tyr Arg Gly Asn Val Ala
            180             185             190

Val Thr Val Ser Gly His Thr Cys Gln His Trp Ser Ala Gln Thr Pro
            195             200             205

His Thr His Asn Arg Thr Pro Glu Asn Phe Pro Cys Lys Asn Leu Asp
        210             215             220

Glu Asn Tyr Cys Arg Asn Pro Asp Gly Lys Arg Ala Pro Trp Cys His
225             230             235             240

Thr Thr Asn Ser Gln Val Arg Trp Glu Tyr Cys Lys Ile Pro Ser Cys
                245             250             255

Asp Ser Ser Pro Val Ser Thr Glu Gln Leu Ala Pro Thr Ala Pro Pro
            260             265             270

Glu Leu Thr Pro Val Val Gln Asp Cys Tyr His Gly Asp Gly Gln Ser
        275             280             285

Tyr Arg Gly Thr Ser Ser Thr Thr Thr Thr Gly Lys Lys Cys Gln Ser
    290             295             300

Trp Ser Ser Met Thr Pro His Arg His Gln Lys Thr Pro Glu Asn Tyr
305             310             315             320

Pro Asn Ala Gly Leu Thr Met Asn Tyr Cys Arg Asn Pro Asp Ala Asp
            325             330             335

Lys Gly Pro Trp Cys Phe Thr Thr Asp Pro Ser Val Arg Trp Glu Tyr
            340             345             350

Cys Asn Leu Lys Lys Cys Ser Gly Thr Glu Ala Ser Val Val Ala Pro
            355             360             365

Pro Pro Val Val Leu Leu Pro Asp Val Glu Thr Pro Ser Glu Glu Asp
        370             375             380

Cys Met Phe Gly Asn Gly Lys Gly Tyr Arg
385             390
```